US011174479B2

(12) United States Patent
Greenleaf et al.

(10) Patent No.: US 11,174,479 B2
(45) Date of Patent: Nov. 16, 2021

(54) DEVICES AND METHODS FOR DISPLAY OF ENCODED PEPTIDES, POLYPEPTIDES, AND PROTEINS ON DNA

(71) Applicant: The Board of Trustees of the Leland Stanford Junior University, Stanford, CA (US)

(72) Inventors: William J. Greenleaf, Redwood City, CA (US); Curtis J. Layton, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 123 days.

(21) Appl. No.: 16/538,640

(22) Filed: Aug. 12, 2019

(65) Prior Publication Data

US 2020/0048629 A1 Feb. 13, 2020

Related U.S. Application Data

(60) Provisional application No. 62/718,320, filed on Aug. 13, 2018.

(51) Int. Cl.
*C12N 15/10* (2006.01)
*C12N 15/67* (2006.01)

(52) U.S. Cl.
CPC ..... *C12N 15/1062* (2013.01); *C12N 15/1041* (2013.01); *C12N 15/1075* (2013.01); *C12N 15/67* (2013.01)

(58) Field of Classification Search
CPC ............ C12N 15/1062; C12N 15/1041; C12N 15/1075; C12N 15/67
See application file for complete search history.

(56) References Cited

U.S. PATENT DOCUMENTS 8,623,629 B2 * 1/2014 Sibbesen et al. ............. 435/200
9,534,217 B2 * 1/2017 Soucaille et al. .. C12N 15/1086
(Continued)

FOREIGN PATENT DOCUMENTS

WO 2012/048340 A2 4/2012
WO WO 2014/189768 A1 * 11/2014

OTHER PUBLICATIONS

Gutierrez et al. "eIF5A Promotes Translation of Polyproline Motifs" Mol Cell. Jul. 11, 2013; 51(1): 35-45. doi:10.1016/j.molcel.2013.04.021 (Year: 2013).*
(Continued)

*Primary Examiner* — Richard A Schnizer
*Assistant Examiner* — K. Lau
(74) *Attorney, Agent, or Firm* — Bozicevic, Field & Francis LLP; Jenny L. Buchbinder

(57) ABSTRACT

A method for displaying proteins and peptides is disclosed in which individual proteins or peptides remain associated with the DNA encoding them. Proteins or peptides can be generated by in vitro translation of DNA templates, either free in solution or arrayed on a solid support, such that the proteins or peptides remain immobilized on their DNA templates. In particular, high throughput sequencing can be combined with high throughput functional characterization of encoded proteins and peptides, wherein the identity of each protein or peptide is determined by DNA sequencing, and functional studies are carried out directly on each protein or peptide while immobilized on the DNA template encoding it. The methods of the invention should find numerous applications, for example, in high throughput genetic or pharmacological screening, epitope mapping, and protein engineering and directed evolution.

30 Claims, 9 Drawing Sheets

Specification includes a Sequence Listing.

(56) References Cited

U.S. PATENT DOCUMENTS

| | | | |
|---|---|---|---|
| 10,011,830 B2* | 7/2018 | Greenleaf et al. | C12N 15/1041 |
| 2001/0046680 A1 | 11/2001 | Yu | |
| 2002/0076692 A1 | 6/2002 | Osbourn et al. | |
| 2004/0091955 A1 | 5/2004 | Forster et al. | |
| 2008/0193921 A1 | 8/2008 | Landick et al. | |
| 2011/0008774 A1 | 1/2011 | Delisa et al. | |
| 2013/0012398 A1 | 1/2013 | Yen et al. | |
| 2013/0288908 A1 | 10/2013 | Fujino et al. | |
| 2015/0057162 A1 | 2/2015 | Ullman | |

OTHER PUBLICATIONS

Foth et al. "Whipworm genome and dual-species transcriptome analyses provide molecular insights into an intimate host-parasite interaction" Nature Genetics vol. 46, No. 7, Jul. 2014 (Year: 2014).*

Castro-Roa et al. (2012) In vitro experimental system for analysis of transcription-translation coupling. Nucleic Acids Res. 40(6):e45.

Hanes et al. (2000) Selecting and evolving functional proteins in vitro by ribosome display. Methods Enzymol. 328:404-430.

Villemagne et al. (2006) Highly efficient ribosome display selection by use of purified components for in vitro translation. J. Immunol. Methods 313(1-2):140-148.

Shah et al. (2007) Full-sequence computational design and solution structure of a thermostable protein variant. J. Mol. Biol. 372(1):1-6.

Murray et al. (2013) Cell-free translation of peptides and proteins: from high throughput screening to clinical production. Curr. Opin. Chem. Biol. 17(3):420-426.

Frieda et al. (2012) Direct observation of cotranscriptional folding in an adenine riboswitch. Science 338(6105):397-400.

Robinson et al. (2008) Expression of human nPTB is limited by extreme suboptimal codon content. PLOS One 3:e1801.

PCT/US2014/038236 International Search Report.

* cited by examiner

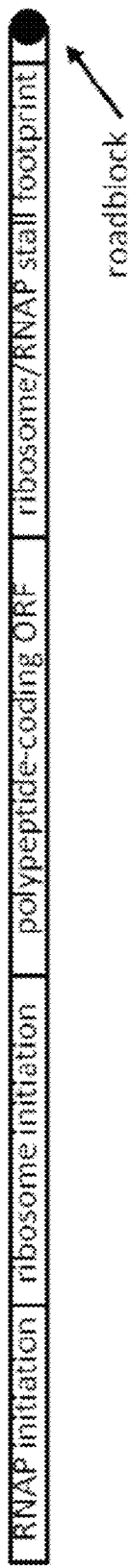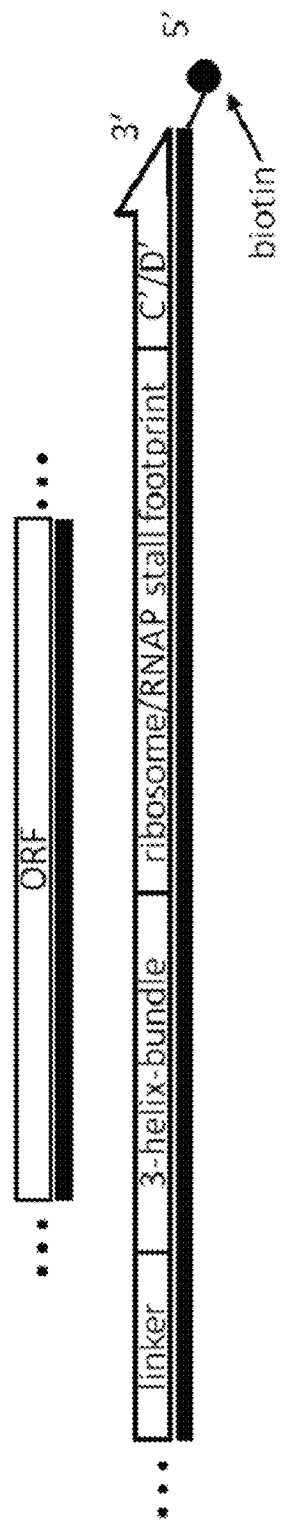
FIG. 1A
FIG. 1B

Fiducial mark signal only anti-FLAG + Alexa555-secondary antibody detection

DEVICES AND METHODS FOR DISPLAY OF ENCODED PEPTIDES, POLYPEPTIDES, AND PROTEINS ON DNA

TECHNICAL FIELD

The present invention pertains generally to devices and methods for protein display. In particular, the invention relates to devices and methods for display of proteins, polypeptides, or peptides on DNA templates encoding them and more specifically to display on a DNA chip.

BACKGROUND

Directed evolution has been performed using various strategies for selection and enrichment of functional molecules from large libraries. Many of these strategies involve the physical linkage of macromolecules to a genetic construct that encodes them. Examples of such strategies include covalent puromycin linkage to RNA in mRNA display (Lipovsek et al. (2004) J. Immunol. Methods 290: 51-67), genetic fusion to a bacteriophage coat protein in phage display (Lowman et al. (1991) Biochemistry 30(45): 10832-10838), and ribosome stalling on RNA in ribosome display (Lipovsek et al., supra; Hanes et al. (2000) Methods Enzymol. 328:404-430).

Protein and peptide arrays can, in principle, be used to query the binding interactions or activities of large numbers of proteins or peptides in parallel. Generally, these arrays are produced by individually synthesizing peptides or expressing and purifying proteins, then printing them onto an array. Recent advances using in situ synthesis by photolithography have increased the throughput of array production (Price et al. (2012) Nat. Med. 18(9):1434-1440), but even so, the processes necessary for protein expression or peptide synthesis are laborious and have limited the throughput of these arrays to at most several thousand individual members. Also, many proteins, when immobilized on a solid surface, are unstable and adsorb onto the surface or aggregate within a short time, limiting the longevity and utility of conventional protein arrays.

Thus, there remains a need for improved methods that would allow display of millions to billions of different functional proteins, polypeptides, peptides, or other ribosomally translated products for high-throughput, massively parallel screening.

SUMMARY

The present invention relates to a novel method for displaying a ribosomal translation product such that the ribosomal translation product remains associated with the DNA encoding it. The ribosomal translation product may include a protein or peptide, a biologically active fragment thereof, or other ribosomal translation product, which can be displayed on a DNA template either free in solution or immobilized on a solid support. The methods of the invention can be readily adapted to perform massively parallel high-throughput protein screening. Accordingly, massively parallel arrays displaying millions to billions of different functional proteins, peptides, or other ribosomally translated molecules can be generated. In particular, high throughput sequencing can be combined with high throughput functional characterization of encoded proteins and peptides, wherein the identity of each array member can be determined by DNA sequencing, and functional studies can be carried out directly on each protein, peptide, or other ribosomal translation product while immobilized in the array. Additionally, arrays may be incorporated into a flow cell or microfluidic device to facilitate high throughput processing.

In one aspect, the invention includes a method for displaying a polypeptide on a DNA template encoding it, the method comprising: a) providing a DNA template that encodes the polypeptide, wherein the DNA template comprises: i) a promoter operably linked to an open reading frame (ORF); ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template antisense strand and the 3' end of the DNA template sense strand; and iii) a nucleic acid encoding a ribosome stall sequence, wherein the nucleic acid encoding the ribosome stall sequence is located on the 3' side of the ORF; b) adding an RNA polymerase that can be blocked by the molecular roadblock, wherein the RNA polymerase binds to the promoter of the DNA template and carries out transcription of the DNA template until the RNA polymerase stalls at the molecular roadblock where the RNA polymerase is blocked from further progress, such that the DNA template and transcribed mRNA remain associated; and c) adding a ribosome that binds to a ribosomal binding site on the mRNA, wherein the ribosome carries out protein translation until the ribosome reaches the ribosome stall sequence, wherein the ribosome is blocked from further progress, such that the ribosome displays the nascent polypeptide while remaining associated with the mRNA. The DNA template may comprise genomic DNA, cDNA, or synthetic DNA. The ORF may further comprise a sequence encoding a linker. Exemplary linker sequences include SEQ ID NO:7 and SEQ ID NO:9. In some embodiments, the promoter comprises the sequence of SEQ ID NO:13 or a sequence having at least 95% identity to the sequence of SEQ ID NO:13. If desired, the single-stranded mRNA, produced by transcription of the DNA template, may be cleaved proximal to the ribosome after the ribosome reaches the molecular roadblock. The molecular roadblock can be any molecule, complex, or chemical modification of the DNA that blocks progress of the RNA polymerase while allowing the RNA polymerase to remain attached to the DNA template. A roadblock can be placed at the 5' end of the antisense DNA strand or the 3' end of the sense DNA strand, or both. In one embodiment, the molecular roadblock is formed by biotinylating the DNA either at the 3' end of the sense strand or the 5' end of the anti-sense strand, followed by binding of streptavidin, wherein the biotin-streptavidin complex serves as a molecular roadblock that blocks the RNA polymerase. The DNA template may further comprise one or more spacer sequences between the different elements of the construct.

In certain embodiments, the DNA template encodes an mRNA having a ribosome stall sequence. In certain embodiments, the ribosome stall sequence comprises a stop codon (e.g., UAG (amber), UAA (ochre), or UGA (opal or umber) in the mRNA). In another embodiment, the ribosome stall sequence further comprises a polyproline-coding sequence adjacent to the stop codon. In one embodiment, the polyproline-coding sequence comprises a coding sequence for a triple-proline motif, wherein the coding sequence for the triple-proline motif is located before (i.e., on the 5' side of) the stop codon. In another embodiment, the ribosome stall sequence further comprises an arginine-histidine-arginine coding sequence adjacent to the polyproline-coding sequence (e.g., triple-proline motif), wherein the argininehistidine-arginine coding sequence is located before (i.e., on the 5' side of) the polyproline-coding sequence.

In certain embodiments, the ribosome stall sequence encodes an amino acid sequence selected from the group consisting of SEQ ID NO:11 and SEQ ID NOS:15-17; or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the ribosome stalls at the stall sequence.

In certain embodiments, the nucleic acid encoding the ribosome stall sequence comprises a nucleotide sequence of SEQ ID NO:12; or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the ribosome stalls at the encoded ribosome stall sequence on the transcribed mRNA.

In certain embodiments, the mRNA further comprises a Shine Dalgarno sequence. In certain embodiments, the Shine Dalgarno sequence comprises the sequence of SEQ ID NO:14; or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the ribosome binds at the ribosomal binding site.

In certain embodiments, protein translation is carried out using an in vitro cell-free expression system. The codon usage in the ORF of the DNA template may be optimized for expression in the particular cell-free expression system chosen for protein translation. In certain embodiments, one or more non-canonical amino acids are incorporated into the translated ribosomal translation product, such as, but not limited to, D-amino acids, beta amino acids, or N-substituted glycines (peptoids).

In certain embodiments, protein translation is carried out using an in vitro cell-free expression system lacking one or more release factors, such that the ribosome is not released from the stop codon on the mRNA. For example, one or more release factors selected from the group consisting of release factor 1 (RF1), release factor 2 (RF2), and release factor 3 (RF3) or all release factors may be absent in the in vitro cell-free expression system. In one embodiment, protein translation is carried out using an in vitro cell-free expression system lacking any release factors.

In one embodiment, the method further comprises providing conditions that allow only one RNA polymerase to initiate transcription on the DNA template. For example, the DNA template may further comprise a stall sequence, wherein the first RNA polymerase to initiate transcription stalls at a position on the DNA template such that initiation of any other polymerase is blocked. An exemplary stall sequence comprises the sequence of SEQ ID NO:4. Transcription is carried out under conditions of nucleotide starvation, wherein the RNA polymerase stalls at a particular position on the DNA template because the nucleotide needed for addition at that position is not provided. After the RNA polymerase stalls, any unbound polymerases are removed, for example, by washing, and then the missing nucleotide needed to resume transcription is added to allow transcription to continue until the one remaining RNA polymerase bound to the DNA template stalls at the molecular roadblock. Alternatively, the unbound RNA polymerases may be inactivated rather than being removed to ensure that only one RNA polymerase remains bound to the DNA template. In one embodiment, heparin is used to inactivate the unbound RNA polymerases.

In another embodiment, the method further comprises providing conditions that allow only one ribosome to initiate translation on the RNA transcript. For example, translation can be carried out under conditions of amino acid starvation, wherein the ribosome stalls at a particular position on the RNA transcript because the amino acid needed for addition at that position is not provided. Then, any unbound ribosomes can be removed, for example, by washing, and the missing amino acid needed to resume translation can be added to allow translation to continue until the one bound ribosome reaches the ribosome stall sequence.

A plurality of proteins or peptides may be displayed simultaneously by this method. For example, this method can be used to display the collective proteins or peptides encoded by a genomic library for an organism or a cDNA library produced from RNA from an organism, or a selected subset of proteins or peptides of interest expressed by an organism, or engineered proteins or peptides. The DNA library used for display may be entirely or partially synthetic and may contain sequences optimized for the expression of a particular set of polypeptides. The plurality of DNA templates may be free in solution or immobilized on a solid support.

A solid support may comprise, for example, glass, quartz, silica, metal, ceramic, plastic, nylon, or polyacrylamide. Exemplary solid supports include a slide, a bead, a multi-well plate, a gel, a membrane, or the inner surface of a flow cell or microchannel. In one embodiment, the DNA templates are immobilized in a polyacrylamide matrix polymerized on the surface of a solid support. DNA templates may be distributed randomly on a solid support or ordered in an array, wherein each DNA template occupies a discrete position on the solid support. The solid support may further comprise capture oligonucleotides or primers attached to the surface capable of hybridizing to the DNA template to facilitate immobilization of the DNA template on the solid support, and optionally amplification and/or sequencing of the DNA template. In one embodiment, the solid support comprises a plurality of bridge PCR primers to allow clonal amplification of DNA templates immobilized on the solid support. In one embodiment, the DNA templates comprise adapter sequences capable of hybridizing to common primers for high-throughput sequencing or amplification.

In one embodiment, the method further comprises amplification of at least one DNA template (e.g., for cloning or sequencing). Amplification may be performed using any known method, such as polymerase chain reaction (PCR) or other nucleic acid amplification process (e.g., ligase chain reaction (LGR), nucleic acid sequence-based amplification (NASBA), transcription-mediated amplification (TMA), Q-beta amplification, strand displacement amplification, or target mediated amplification). In one embodiment, amplification comprises performing a clonal amplification method, such as, but not limited to bridge amplification, emulsion PCR (ePCR), or rolling circle amplification.

In another embodiment, the method further comprises sequencing at least one DNA template. In one embodiment, the plurality of DNA templates is sequenced by a high-throughput DNA sequencing method. For example, each DNA template may comprise a pair of adapter sequences at the 5' and 3' ends of the DNA template to allow sequencing or amplification of multiple DNA templates simultaneously by the same set of primers. Exemplary adapter sequences comprise the sequences of SEQ ID NO:1 and SEQ ID NO:2.

In one embodiment, the sequencing adapters comprise paired-end sequencing adapters.

In another embodiment, the invention includes a protein array produced by the methods described herein. The protein array may comprise a plurality of displayed polypeptides comprising, for example, a library of antigens, antibodies, enzymes, substrates, or receptors. The protein array may be contained inside a flow cell or a microfluidic device. Such arrays can be used, for example, in high throughput genetic or pharmacological screening, epitope mapping, or protein engineering.

In another embodiment, the invention includes a method of performing epitope mapping, the method comprising: a) providing a plurality of DNA templates encoding peptide fragments of a protein; b) displaying the peptide fragments according to the methods described herein; and c) detecting binding of an antibody to at least one peptide fragment in order to identify an epitope of the protein that binds to the antibody.

In another embodiment, the invention includes a method of profiling an immune response of a subject, the method comprising: a) providing a plurality of DNA templates each encoding a different target antigen of interest; displaying each target antigen according to the methods described herein; b) obtaining a biological sample (e.g., blood) from the subject; and c) detecting binding of at least one antibody or lymphocyte from the biological sample to at least one target antigen of interest. One or more antibodies (e.g., autoantibodies or antibodies to a particular antigen or set of antigens), T cells, or B cells produced by an immune response may be detected.

In another embodiment, the invention includes a method of screening a library of polypeptides for the ability to bind to a target molecule, the method comprising:

a) providing a plurality of DNA templates collectively encoding the library of polypeptides; b) displaying each polypeptide according to a method described herein; c) contacting the plurality of polypeptides with the target molecule; and d) identifying at least one displayed polypeptide that binds to the target molecule. In certain embodiments, the target molecule is selected from the group consisting of a receptor, a ligand, an antibody, an antigen, an enzyme, a transporter, a substrate, an inhibitor, an activator, a cofactor, a drug, a nucleic acid, a lipid, a carbohydrate, a glycoprotein, an extracellular matrix component, a small organic molecule, and an inorganic molecule. The target molecule may comprise a detectable label to allow detection of binding of the target molecule to at least one displayed polypeptide. Binding of a target molecule to displayed polypeptides may further be characterized quantitatively. The method may further comprise enriching the DNA library for DNA templates encoding polypeptides that bind to the target molecule or depleting the DNA library of DNA templates encoding polypeptides that do not bind to the target molecule or that have undesired activities.

In another embodiment, the invention includes a method of screening a library of polypeptides for biological activity in the presence of a target molecule, the method comprising: a) providing a plurality of DNA templates collectively encoding the library of polypeptides; b) displaying each polypeptide according to a method described herein; c) contacting the plurality of polypeptides with the target molecule; d) assaying for biological activity in the presence of the target molecule, and e) identifying at least one displayed polypeptide that has biological activity. Exemplary biological activities that may be assayed include enzymatic activity, substrate activity, ligand-binding activity, transport activity, agonist activity, or antagonist activity. In certain embodiments, the target molecule is selected from the group consisting of a receptor, a ligand, an antibody, an antigen, an enzyme, a transporter, a substrate, an inhibitor, an activator, a cofactor, a drug, a nucleic acid, a lipid, a carbohydrate, a glycoprotein, an extracellular matrix component, a small organic molecule, and an inorganic molecule. The method may further comprise enriching the DNA library for DNA templates encoding polypeptides that have biological activity in the presence of the target molecule, or depleting the DNA library of DNA templates encoding polypeptides that do not have the desired activity or that have undesired activities.

In another embodiment, the invention includes a method of performing directed evolution of a protein, the method comprising: a) providing a plurality of DNA templates comprising a library of gene variants encoding a plurality of protein variants; b) displaying the plurality of protein variants as described herein, wherein each DNA template comprises: i) a promoter operably linked to an open reading frame (ORF); ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template antisense strand and the 3' end of the DNA template sense strand; and iii) a nucleic acid encoding a ribosome stall sequence, wherein the nucleic acid encoding the ribosome stall sequence is located on the 3' side of the ORF; c) assaying the plurality of protein variants for a desired biological activity; d) selecting protein variants that have the desired biological activity; d) mutating the DNA sequences of the DNA templates encoding said protein variants that have the desired biological activity; and f) further selecting protein variants that have the desired biological activity to generate a DNA library enriched for DNA templates encoding protein variants that have the desired biological activity. In one embodiment, the method further comprises sequencing at least one DNA template to determine the sequence of a DNA template encoding a protein variant with a desired biological activity. The library of gene variants may be created, for example, using error-prone PCR or DNA shuffling. In one embodiment, the method further comprises depleting the library of DNA templates encoding protein variants with undesired activities.

These and other embodiments of the subject invention will readily occur to those of skill in the art in view of the disclosure herein.

BRIEF DESCRIPTION OF THE FIGURES

FIGS. 1A and 1B show schematic representations of the DNA sequence elements used to display a protein or peptide on the template that encodes it. FIG. 1A shows a construct comprising an RNA polymerase (RNAP) binding site, a ribosome initiation site, an open reading frame (ORF) encoding a polypeptide, a ribosome/RNAP stall site, and a 3'-roadblock (black circle). FIG. 1B shows one implementation used for generation of a protein/peptide array on a high-throughput sequencing flow cell. The DNA template is ready to be clonally amplified and sequenced on a sequencer, transcribed with *E. coli* RNA polymerase holoenzyme (σ-70 saturated), and transcribed with a bacterial cell-free translation system.

8. Translation and stalling of the ribosome to display the encoded protein product on-chip (not shown—cleavage of the single-stranded RNA transcript to prevent RNA from participating in functional protein assays).

Figure 2:
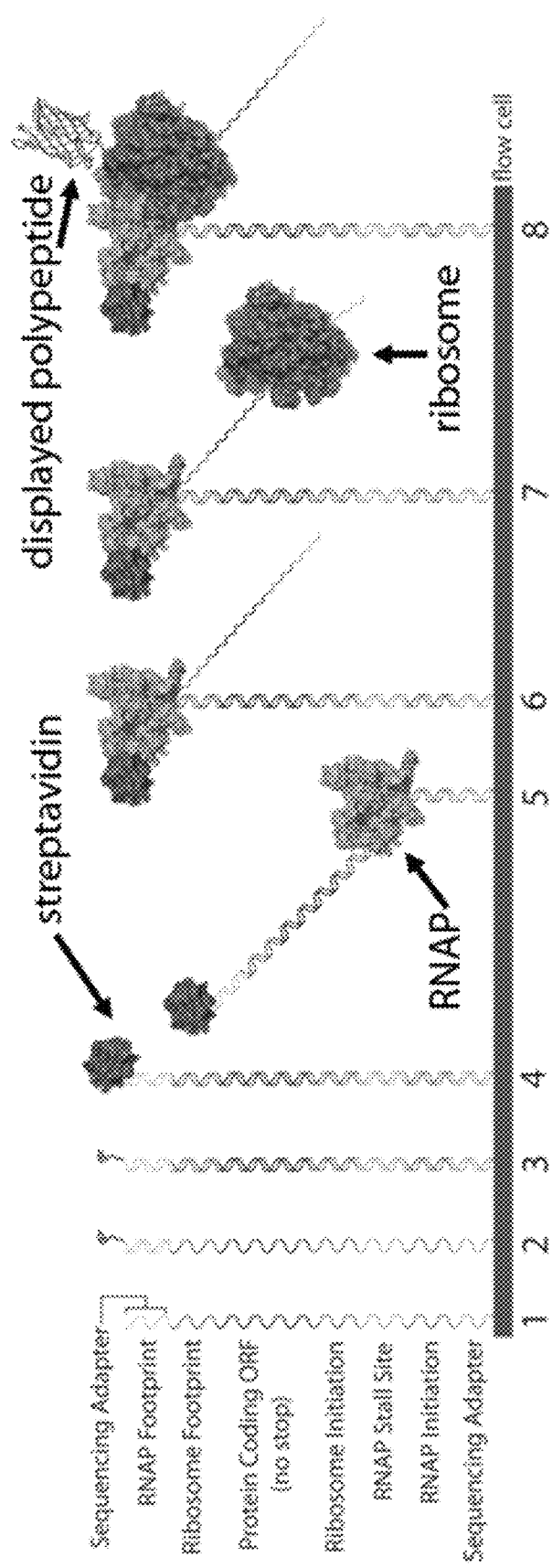
FIG. 2 shows the steps for in situ generation of a massively parallel protein array on a high throughput sequencing instrument: 1. ssDNA library, clustered and sequenced on an Illumina flow cell. 2. Hybridization of a biotinylated primer. 3. Extension to produce double-stranded DNA. 4. Binding of the streptavidin roadblock. 5. Initiation of *E. coli* RNAp and stalling (washing ensures one polymerase per template). 6. Transcription is resumed by adding the depleted nucleotide and the resulting transcript remains associated in a stable ternary complex at the roadblock. 7. Initiation of the ribosome on the immobilized transcript.
Figure 3:
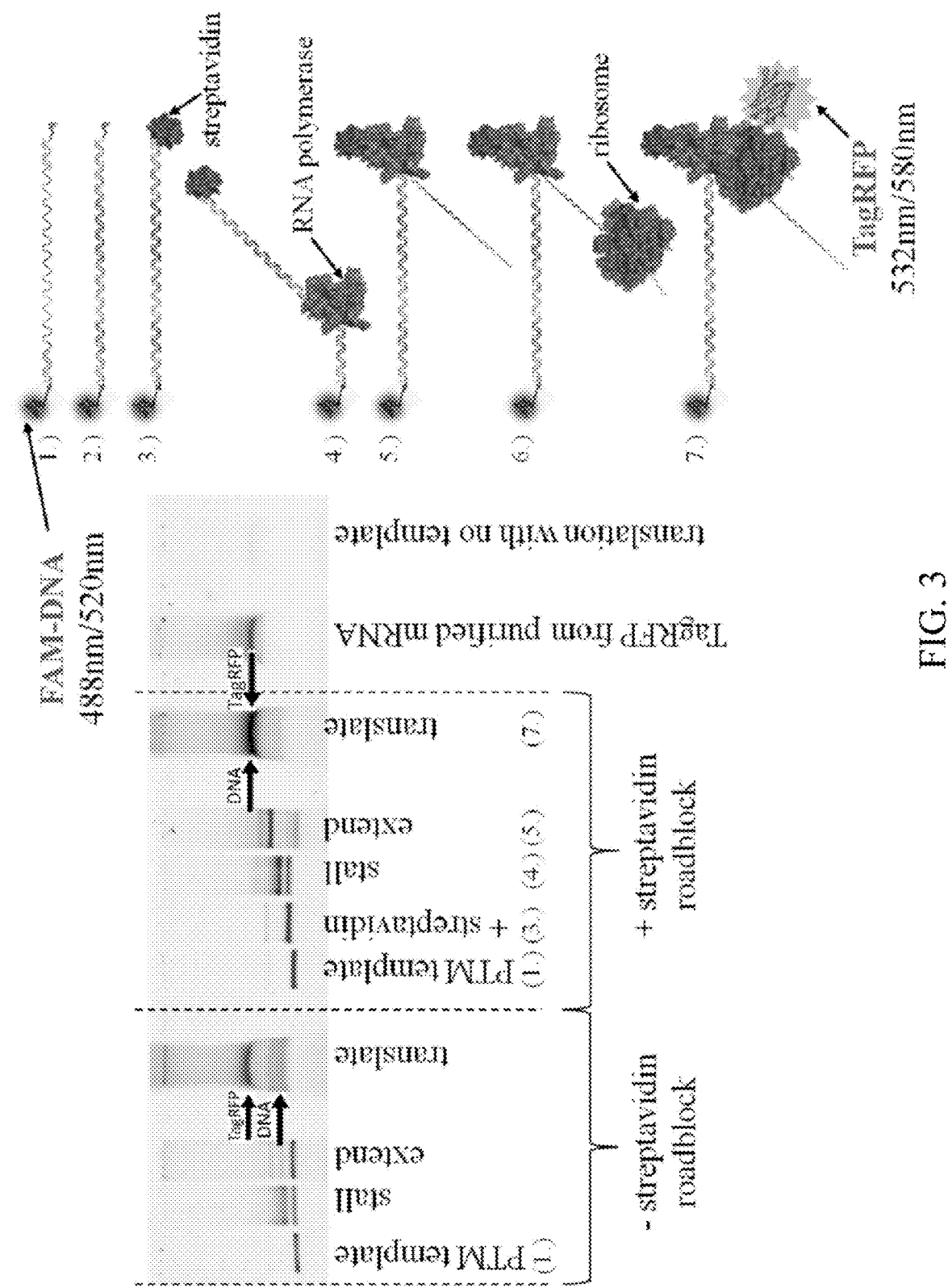

FIG. 3 shows an encoded red fluorescent protein is expressed in vitro using the methods of the invention and remains associated with its DNA template, as evidenced by co-localization during gel electrophoresis (1% agarose gel, 1×TBE). The steps are essentially the same as in FIG. 2, except that the template is labeled with fluorescein amidite (FAM) and is not immobilized. Without streptavidin roadblock—the RNA dissociates from the DNA on extension, and translation results in separate bands for DNA and protein. With streptavidin roadblock—the RNA remains associated with the DNA template on extension, and translation results in co-localization of DNA and protein. Black indicates overlap of the red (protein) and green (DNA) channels. The laser excitation/emission filter combinations were imaged separately on a GE Healthcare TYPHOON fluorescence scanner, falsely colored as indicated, and superimposed.

Figure 4:
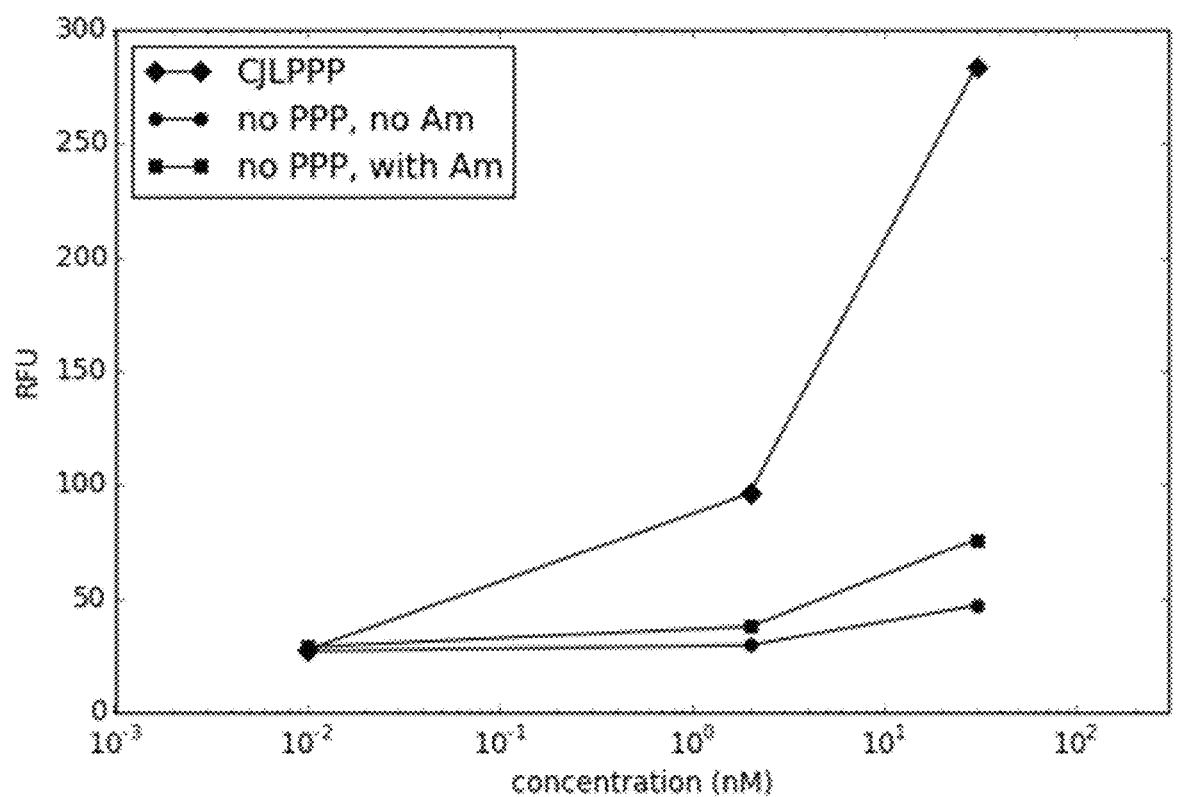

FIG. 4 shows results with constructs that displayed 2×FLAG® tag, varying only by the stall sequence, which were used to generate peptides on chip, then interrogated with M2 anti-FLAG® tag antibody and a fluorescent secondary at both 2 nM and 30 nM. The stall sequence leads to significantly better display of the peptide. The Amber stop codon alone is not sufficient for efficient display; the sequence of the CJL-PPP sequence does, in fact, induce stable ribosomal stalling.

Figure 5:
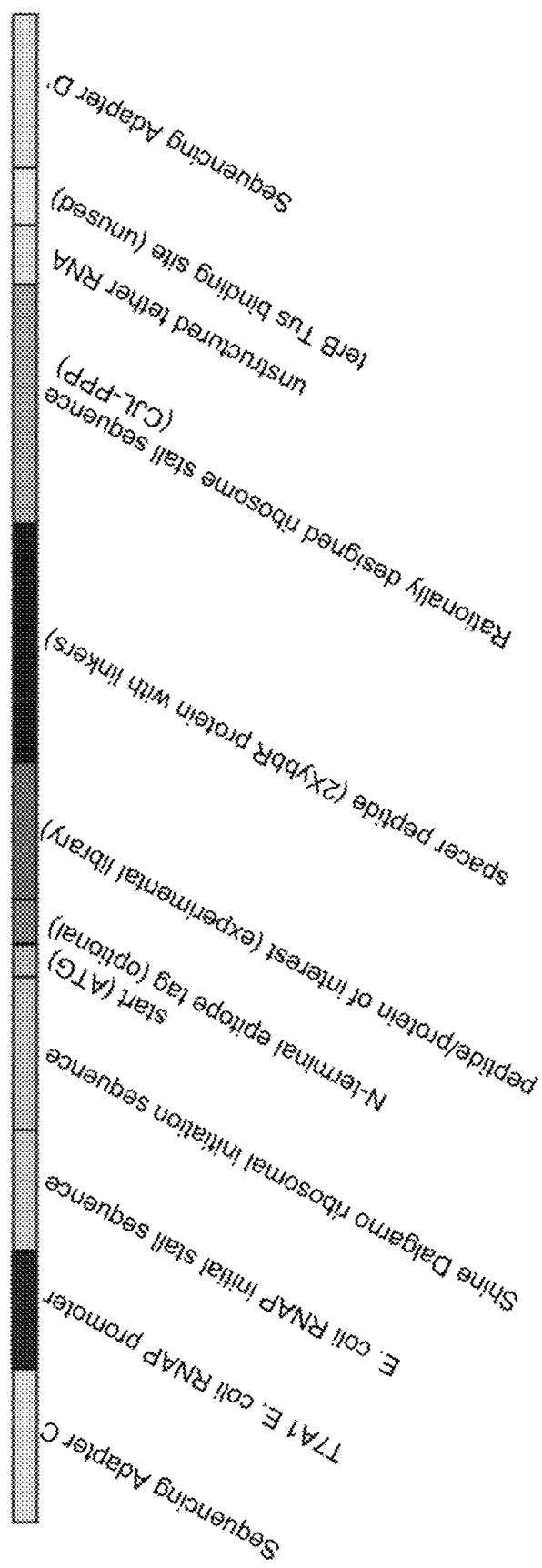

FIG. 5 shows the construct structure used for display as described in FIG. 4.

Figure 6A:
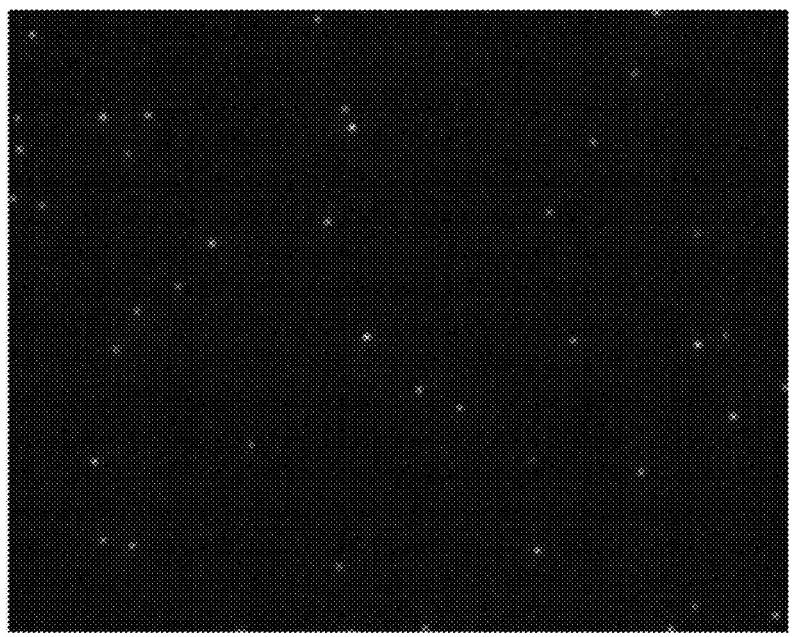
Figure 6A:
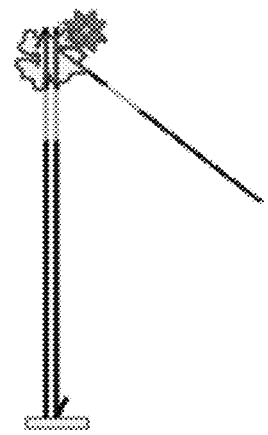
Figure 6B:
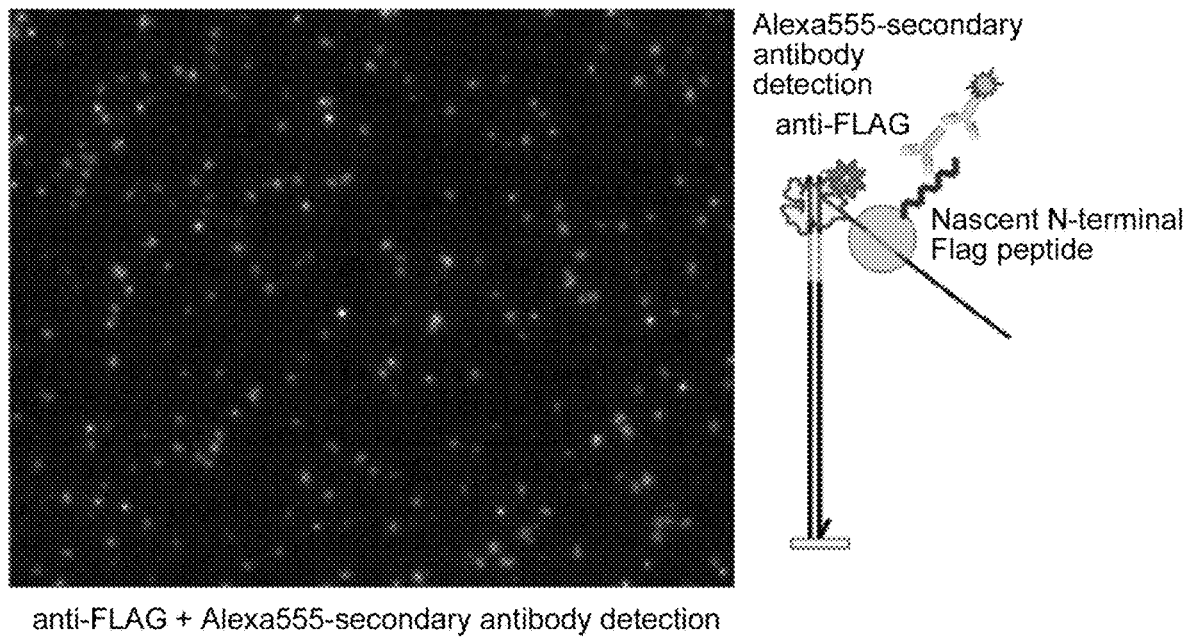

FIGS. 6A and 6B show images showing stable generation of the FLAG® tag peptide on chip. FIG. 6A shows fiducial mark signal only. FIG. 6B shows detection with an anti-FLAG® tag antibody and fluorescent secondary antibody.

Figure 7:
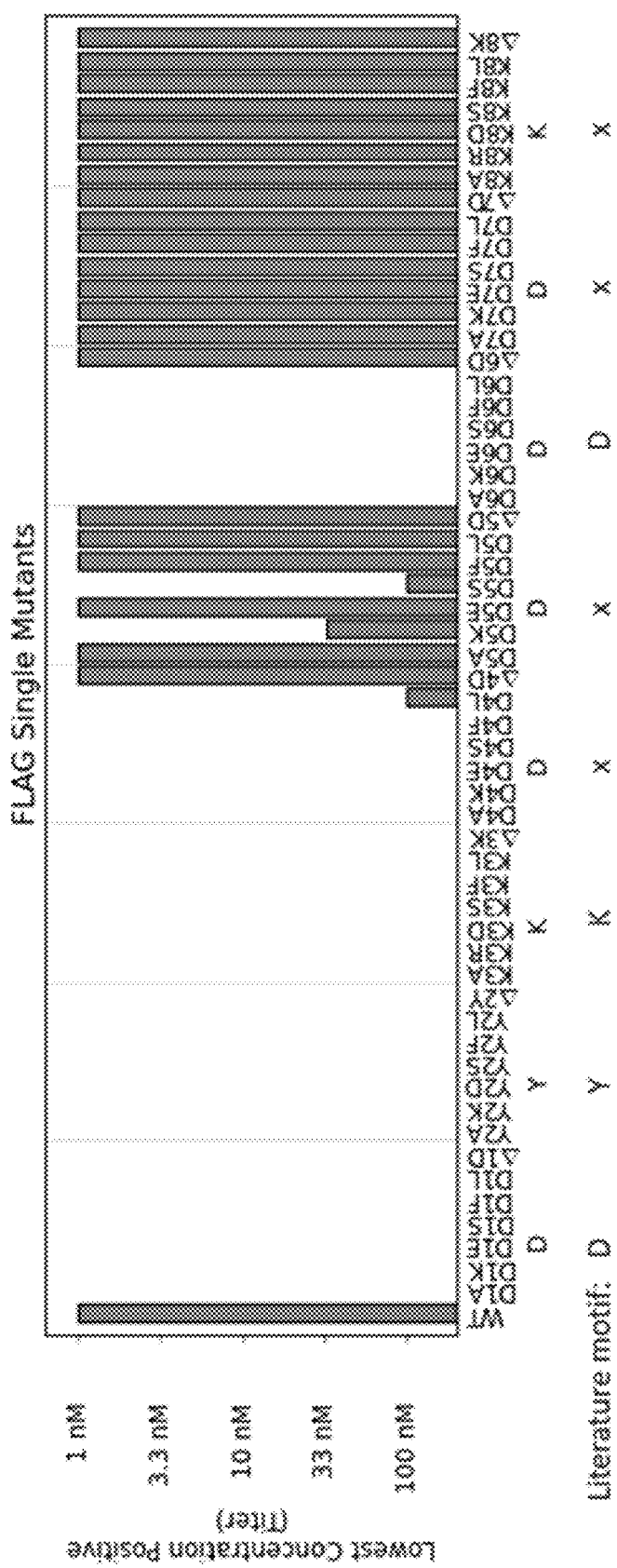

FIG. 7 shows that titer values obtained from functional protein array analysis of M2 anti-FLAG® tag antibody binding to FLAG® tag mutants agree with the expected literature motif.

Figure 8:
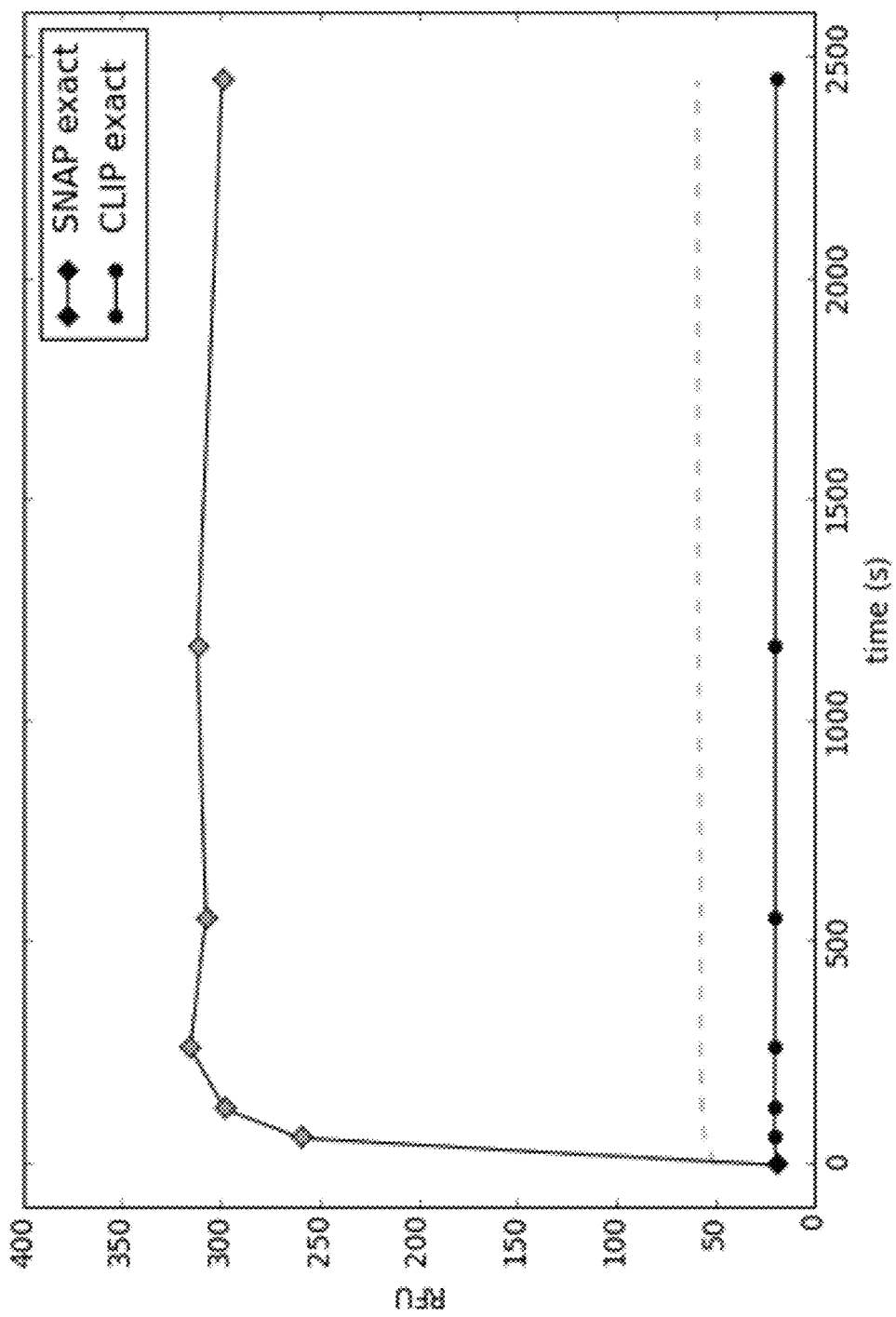

FIG. 8 shows the labeling time course with 1 µM SNAP-Surface 549® red fluorescent substrate of variants displayed on-chip. CLIP-tag™ human 06-alkylguanine-DNA-alkyltransferase variant tag is variant protein that differs by only 8 mutations that is not expected to self-label with SNAP-surface 549® red fluorescent substrate. Each point is the mean of several thousand clusters where the template DNA exactly encodes each protein of interest. The dashed line indicates a fluorescence threshold for labeled clusters based on a 1% rate of random discovery.

DETAILED DESCRIPTION

The practice of the present invention will employ, unless otherwise indicated, conventional methods of DNA sequencing, proteomics, biochemistry, molecular biology, and recombinant DNA techniques, within the skill of the art. Such techniques are explained fully in the literature. See, e.g., High-Throughput Next Generation Sequencing: Methods and Applications (Methods in Molecular Biology, Y. M. Kwon and S. C. Ricke eds., Humana Press, 2011; High-Throughput Screening in Drug Discovery (Methods and Principles in Medicinal Chemistry, J. Hüser, R. Mannhold, H. Kubinyi, and G. Folkers eds., Wiley-VCH; 1st edition, 2006); J. P. Devlin High Throughput Screening: The Discovery of Bioactive Substances (CRC Press; 1st edition, 1997); Protein Arrays, Biochips, and Proteomics (J. S. Albala and I. Humphery-Smith eds., Marcel Dekker, 1st edition, 2003); Protein Arrays: Methods and Protocols (Methods in Molecular Biology, E. Fung ed., Humana Press; 2004); Proteomics: Methods and Protocols (Methods in Molecular Biology, J. Reinders and A. Sickmann eds., Humana Press; 2009); A. L. Lehninger, Biochemistry (Worth Publishers, Inc., current addition); Sambrook, et al., Molecular Cloning: A Laboratory Manual (3rd Edition, 2001); Methods In Enzymology (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a protein" includes a mixture of two or more proteins, and the like.

The term "about," particularly in reference to a given quantity, is meant to encompass deviations of plus or minus five percent.

The terms "polypeptide," "peptide," "oligopeptide," and "protein," as used herein generally refer to any compound comprising naturally occurring or synthetic amino acid polymers or amino acid-like molecules including but not limited to compounds comprising amino and/or imino molecules. No particular size is implied by use of the term "peptide", "oligopeptide", "polypeptide", or "protein" and these terms are used interchangeably. The term, "protein," as used herein refers to a full-length protein, portion of a protein, or a peptide. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring (e.g., synthetic). Thus, synthetic oligopeptides, dimers, multimers (e.g., tandem repeats, multiple antigenic peptide (MAP) forms, linearly-linked peptides), cyclized, branched molecules and the like, are included within the definition. The terms also include molecules comprising one or more peptoids (e.g., N-substituted glycine residues) and other synthetic amino acids or peptides (see, e.g., U.S. Pat. Nos. 5,831,005; 5,877,278; and 5,977,301; Nguyen et al. (2000) Chem. Biol. 7(7):463-473; and Simon et al. (1992) Proc. Natl. Acad. Sci. USA 89(20):9367-9371 for descriptions of peptoids). Non-limiting lengths of peptides suitable for use in the present invention includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length. Typically, polypeptides useful in this invention can have a maximum length suitable for the intended application. Further, polypeptides as described herein, for example synthetic polypeptides, may include additional molecules such as labels or other chemical moieties. Such moieties may further enhance interaction of the peptides with a ligand and/or further detection of a polypeptide being displayed.

Thus, reference to proteins, polypeptides, or peptides also includes derivatives of the amino acid sequences, including one or more non-naturally occurring amino acids. A first polypeptide is "derived from" a second polypeptide if it is (i) encoded by a first polynucleotide derived from a second polynucleotide encoding the second polypeptide, or (ii) displays sequence identity to the second polypeptide as described herein. Sequence (or percent) identity can be determined as described below. Preferably, derivatives exhibit at least about 50% percent identity, more preferably at least about 80%, and even more preferably between about 85% and 99% (or any value therebetween) to the sequence from which they were derived. Such derivatives can include postexpression modifications of the polypeptide, for example, glycosylation, acetylation, phosphorylation, and the like.

Amino acid derivatives can also include modifications to the native sequence, such as deletions, additions and substitutions (generally conservative in nature), so long as the polypeptide maintains the desired activity. These modifications may be deliberate, as through site-directed mutagenesis, or may be accidental, such as through mutations of hosts that produce the proteins or errors due to PCR amplification. Furthermore, modifications may be made that have one or more of the following effects: increasing efficiency of display, in vitro translation, or stability of the polypeptide.

As used herein, the term "biologically active," refers to a protein or peptide, or fragment thereof, having structural, regulatory, or biochemical functions of a naturally occurring molecule. For example, a biologically active fragment could include a functional protein domain exhibiting enzymatic activity (e.g., kinase, protease, phosphatase, glycosidase, acetylase, or transferase) or binding activity (e.g., binding DNA, RNA, protein, hormone, ligand, or antigen).

The term "array" refers to a population of different reaction sites, which can be present on one or more supports, such that the different reaction sites can be differentiated from each other according to their relative location. Typically, a single species of protein displayed on DNA is attached at each individual reaction site. However, multiple copies of a particular species of protein can be attached at a particular reaction site. The array taken as a whole will typically include a plurality of different proteins attached at a plurality of different sites. The reaction sites can be located at different addressable locations on the same support. Alternatively, an array can include separate supports, such as beads, each bearing different reaction sites.

As used herein, a "solid support" refers to a solid surface, such as, but not limited to a plate, slide, wafer, bead, rod, particle, strand, disc, membrane, film, or the inner surface of a flow cell device or microfluidic device. A solid support may comprise various materials, including, but not limited to glass, quartz, silica, metal, ceramic, plastic, nylon, polyacrylamide, resin, hydrogel, and composites thereof. Additionally, a substrate may be added to the surface of a solid support to facilitate attachment of DNA templates (e.g., polyacrylamide matrix for immobilization of DNA templates carrying a terminal acrylamide group).

The term "roadblock" or "molecular roadblock" refers to a configuration of one or more molecules downstream of a transcribable region of DNA positioned such that when an RNA polymerase in the process of transcription encounters the roadblock, the polymerase stalls, forming a stable complex comprising the RNA polymerase and the DNA template and nascent RNA transcript. The roadblock may be a molecular entity, associated covalently or non-covalently with the DNA, or a chemical modification to the DNA, such as a chemical crosslink between strands of DNA that causes the RNA polymerase to stall. The roadblock can be placed at the 5' end of the antisense DNA strand or the 3' end of the sense DNA strand, or both. The roadblock may also include a molecule that binds selectively to a particular sequence of DNA at the appropriate location.

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization, or formamide. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis.

As used herein, the term "capture oligonucleotide" refers to an oligonucleotide that contains a nucleic acid sequence complementary to a nucleic acid sequence present in a target nucleic acid (e.g., DNA template used for displaying a polypeptide) such that the capture oligonucleotide can "capture" the target nucleic acid. One or more capture oligonucleotides can be used in order to capture the target nucleic acid. The polynucleotide regions of a capture oligonucleotide may be composed of DNA, and/or RNA, and/or synthetic nucleotide analogs. Typically, the capture molecule is associated with a solid support, either directly or indirectly.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with a target (template), such complexes (or hybrids) are sufficiently stable to serve the priming function required by, e.g., the DNA polymerase to initiate DNA synthesis.

As used herein, the term "ligand" refers to a molecule that binds to another molecule, e.g., an antigen binding to an antibody, a hormone or neurotransmitter binding to a receptor, or a substrate or allosteric effector binding to an enzyme and includes natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

By "isolated" is meant, when referring to a polypeptide or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The terms "label" and "detectable label" refer to a molecule capable of detection, including, but not limited to, radioactive isotopes, stable (non-radioactive) heavy isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to radiolabels (e.g., 3H, 125I, 35S, 14C, or 32P), stable (non-radioactive) heavy isotopes (e.g., 13C or 15N), phycoerythrin, fluorescein, 7-nitrobenzo-2-oxa-1,3-diazole (NBD), YPet, CyPet, Cascade blue, allophycocyanin, ALEXA® fluorescent dyes (e.g., ALEXA® FLUOR 350 fluorescent dye, ALEXA® FLUOR 430 fluorescent dye, ALEXA® FLUOR 488 fluorescent dye, ALEXA® FLUOR 532 fluorescent dye, ALEXA® FLUOR 546 fluorescent dye, ALEXA® FLUOR 555 fluorescent dye, ALEXA® FLUOR 594 fluorescent dye, ALEXA® FLUOR 647 fluorescent dye, ALEXA® FLUOR 660 fluorescent dye, ALEXA® FLUOR 680 fluorescent dye, ALEXA® FLUOR 750 fluorescent dye), ATTO fluorescent dyes (e.g., ATTO 488 fluorescent dye, ATTO 532 fluorescent dye, ATTO 550 fluorescent dye, ATTO 565 fluorescent dye, ATTO 590 fluorescent dye, ATTO 610 fluorescent dye, ATTO 620 fluorescent dye, ATTO 635 fluorescent dye, ATTO 647 fluorescent dye, ATTO 655 fluorescent dye, and ATTO 680 fluorescent dye), Cy3, Cy5, Cy7, TYE 563 fluorescent dye, TYE 665 fluorescent dye, TYE 705 fluorescent dye, TEX 615 fluorescent dye, JOE fluorescent dye, TET fluorescent dye, HEX fluorescent dye, TAMRA fluorescent dye, ROX fluorescent dye, rhodamine, dansyl, umbelliferone, Texas red, luminol, acradimum esters, biotin or other streptavidin-binding proteins, magnetic beads, electron dense reagents, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, firefly luciferase, *Renilla* luciferase, NADPH, beta-galactosidase, horseradish peroxidase, glucose oxidase, alkaline phosphatase, chloramphenicol acetyl transferase, and urease. Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., QDOT® nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., submicron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "coding sequence" or a sequence which "encodes" a selected polypeptide is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The terms "variant," "analog" and "mutein" refer to biologically active derivatives of the reference molecule. In general, the terms "variant" and "analog" refer to compounds having a native polypeptide sequence and structure with one or more amino acid additions, substitutions, and/or deletions, relative to the native molecule, and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides (see, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention relates to a method for displaying a protein or peptide such that the protein or peptide remains associated with the DNA encoding it. Proteins or peptides can be generated by in vitro translation of DNA templates, either free in solution or arrayed on a solid support, such that the proteins or peptides remain immobilized on the DNA template encoding them (see Example 1). In particular, large protein or peptide arrays can be generated by this method, for example, on the same solid support used to do high-throughput sequencing. The identity of each array member can be determined by DNA sequencing, and functional studies of each encoded protein or peptide may be carried out directly on the proteins or peptides while immobilized on the solid support. Additionally, arrays may be incorporated into a flow cell or microfluidic device to facilitate high throughput processing. Thus, the methods of the invention allow high throughput sequencing to be readily combined with high throughput functional characterization of encoded proteins and peptides and should find numerous applications, for example, in high throughput genetic or pharmacological screening, epitope mapping, and protein engineering and directed evolution.

In order to further an understanding of the invention, a more detailed discussion is provided below regarding methods of displaying proteins or peptides on the DNA encoding them, methods of producing arrays of displayed proteins or peptides, and methods of high throughput screening of displayed proteins or peptides.

A. Displaying Ribosomal Translation Products on DNA

In one aspect, the invention includes a method for displaying a ribosomal translation product (e.g., a protein or peptide, a biologically active fragment thereof, or other ribosomally translated molecule) on a DNA template encoding it. In particular, the DNA template comprises a promoter operably linked to an open reading frame (ORF) and further comprises a molecular roadblock that blocks progress of an RNA polymerase during transcription of the DNA template. The molecular roadblock causes the RNA polymerase to stall during transcription, such that the DNA template and transcribed mRNA remain associated. During translation of the RNA transcript, the stalled RNA polymerase at the molecular roadblock blocks ribosomes from continuing translation, such that the ribosomes display the nascent peptide chain (e.g., protein or peptide, biologically active fragment thereof, or other ribosomally translated molecule) while remaining associated with the RNA transcript. If desired, the single-stranded mRNA, produced by transcription of the DNA template, may be cleaved proximal to the ribosome after the ribosome reaches the molecular roadblock.

The molecular roadblock may comprise a configuration of one or more molecules downstream of a transcribable region of DNA positioned such that when the RNA polymerase in the process of transcription encounters the roadblock, the polymerase stalls, forming a stable complex comprising the RNA polymerase, DNA template, and nascent RNA transcript. The roadblock may be a molecular entity, associated covalently or non-covalently with the DNA, or a chemical modification to the DNA, such as a chemical crosslink between strands of DNA that causes the RNA polymerase to stall. The roadblock can be placed at the 5' end of the antisense DNA strand or the 3' end of the sense DNA strand, or both. The roadblock may also include a molecule that binds selectively to a particular sequence of DNA at the appropriate location. In one embodiment, the molecular roadblock is formed by biotinylating the DNA either at the 3' end of the sense strand or the 5' end of the anti-sense strand, followed by binding of streptavidin, wherein the biotin-streptavidin complex serves as a molecular roadblock that blocks the RNA polymerase.

In addition, the DNA template may encode an mRNA having a ribosome stall sequence. In certain embodiments, the ribosome stall sequence comprises a stop codon (e.g., UAG (amber), UAA (ochre), or UGA (opal or umber) in the mRNA). In another embodiment, the ribosome stall sequence further comprises a polyproline-coding sequence adjacent to the stop codon. In one embodiment, the polyproline-coding sequence comprises a coding sequence for a triple-proline motif, wherein the coding sequence for the triple-proline motif is located before (i.e., on the 5' side of) the stop codon. In another embodiment, the ribosome stall sequence further comprises an arginine-histidine-arginine coding sequence adjacent to the polyproline-coding sequence (e.g., triple-proline motif), wherein the arginine-histidine-arginine coding sequence is located before (i.e., on the 5' side of) the polyproline-coding sequence.

In certain embodiments, the ribosome stall sequence encodes an amino acid sequence selected from the group consisting of SEQ ID NO:11 and SEQ ID NOS:15-17; or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the ribosome stalls at the stall sequence.

In certain embodiments, the nucleic acid encoding the ribosome stall sequence comprises a nucleotide sequence of SEQ ID NO:12; or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the ribosome stalls at the encoded ribosome stall sequence on the transcribed mRNA.

In certain embodiments, the mRNA further comprises a Shine Dalgarno sequence. The Shine Dalgarno sequence may be optimized for a particular ORF of interest to promote efficient ribosome binding and translation initiation. In certain embodiments, the optimized Shine Dalgarno sequence comprises the sequence of SEQ ID NO:14; or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the ribosome binds at the ribosomal binding site.

DNA templates used in the practice of the invention can be derived from any nucleic acid of known or unknown sequence, and can be, for example, a fragment of genomic DNA or cDNA. For example, DNA templates can be derived from a primary nucleic acid sample that has been randomly fragmented. DNA templates can also be obtained from a primary RNA sample by reverse transcription into cDNA. Individual DNA templates may contain a whole gene or part of a gene or cDNA derived from mRNA that encodes a protein or peptide, or a biologically active polypeptide or peptide fragment thereof. Additionally, DNA templates may comprise recombinant engineered constructs.

Protein translation may be carried out using an in vitro cell-free expression system. Translation can be performed in vitro using a crude lysate from any organism that provides all the components needed for translation, including, enzymes, tRNA and accessory factors (excluding release factors), amino acids and an energy supply (e.g., GTP). Cell-free expression systems derived from *Escherichia coli*, wheat germ, and rabbit reticulocytes are commonly used. *E. coli*-based systems provide higher yields, but eukaryotic-based systems are preferable for producing post-translationally modified proteins. Alternatively, artificial reconstituted cell-free systems may be used for protein production. For optimal protein production, the codon usage in the ORF of the DNA template may be optimized for expression in the particular cell-free expression system chosen for protein translation. In addition, labels or tags can be added to proteins to facilitate high-throughput screening. See, e.g., Katzen et al. (2005) Trends Biotechnol. 23:150-156; Jermutus et al. (1998) Curr. Opin. Biotechnol. 9:534-548; Nakano et al. (1998) Biotechnol. Adv. 16:367-384; Spirin (2002) Cell-Free Translation Systems, Springer; Spirin and Swartz (2007) Cell-free Protein Synthesis, Wiley-VCH; Kudlicki (2002) Cell-Free Protein Expression, Landes Bioscience; herein incorporated by reference in their entireties.

In certain embodiments, protein translation is carried out using an in vitro cell-free expression system lacking one or more release factors, such that the ribosome is not released from the stop codon on the mRNA. One or more of the release factors, including release factor 1 (RF1), release factor 2 (RF2), and release factor 3 (RF3) may be absent, or all the release factors may be absent in the in vitro cell-free expression system. The release factors that need to be absent will depend on the stop codon chosen for inclusion in the stall sequence. For example, RF1 normally mediates release of a ribosome from the RNA transcript at an amber codon. Accordingly, if an amber codon is included in the stall sequence, RF1 is omitted from the in vitro cell-free expression system. On the other hand, RF2 normally mediates release of a ribosome from an RNA transcript at either an ochre or opal codon. Therefore, RF2 is omitted from the in vitro cell-free expression system if an ochre or opal codon is included in the stall sequence. In one embodiment, protein translation is carried out using an in vitro cell-free expression system lacking any release factors.

In certain embodiments, one or more non-canonical amino acids are incorporated into the ribosomal translation product, such as, but not limited to, D-amino acids, beta amino acids, or N-substituted glycines (peptoids). Non-canonical amino acids can be introduced into a protein or peptide in either a residue-specific or site-specific fashion. See, e.g., Link et al. (2003) Curr. Opin. Biotechnol. 14(6): 603-609; Johnson et al. (2010) Curr. Opin. Chem. Biol. 14(6):774-780; Zheng et al. (2012) Biotechnol J. 7(1):47-60; herein incorporated by reference.

In one embodiment, the method further comprises providing conditions that allow only one RNA polymerase to initiate transcription on a DNA template. For example, the DNA template may further comprise a stall sequence, wherein the first RNA polymerase to initiate transcription stalls at a position on the DNA template such that initiation of any other polymerase is blocked. An exemplary stall sequence comprises the sequence of SEQ ID NO:4. Transcription is carried out under conditions of nucleotide starvation, wherein the RNA polymerase stalls at a particular position on the DNA template because the nucleotide needed for addition at that position is not provided (see, e.g., Greenleaf and Block (2006) Science 313(5788):801; herein incorporated by reference). After the RNA polymerase stalls, any unbound polymerases are removed, for example, by washing, and then the missing nucleotide needed to resume transcription is added to allow transcription to continue until the one remaining RNA polymerase bound to the DNA template stalls at the molecular roadblock. Alternatively, the unbound RNA polymerases may be inactivated (e.g., using heparin) rather than being removed to ensure that only one RNA polymerase remains bound to the DNA template.

In another embodiment, the method further comprises providing conditions that allow only one ribosome to initiate translation on the RNA transcript. For example, translation can be carried out under conditions of amino acid starvation, wherein the ribosome stalls at a particular position on the RNA transcript because the amino acid needed for addition at that position is not provided. Then, any unbound ribosomes can be removed, for example, by washing, and the missing amino acid needed to resume translation can be added to allow translation to continue until the one bound ribosome reaches the ribosome stall sequence.

The ribosomal translation product may comprise one or more linkers, for example, to facilitate display on a ribosome, cloning, purification, or detection, or to improve solubility. Short flexible linkers having, e.g., 20 or fewer amino acids (i.e., 20, 19, 18, 17, 16, 15, 14, 13, 12, 11, 10, 9, 8, 7, 6, 5, 4, 3, 2, or 1) are useful for separating domains in fusion constructs. Examples include short peptide sequences such as poly-glycine linkers (Glyn where n=2, 3, 4, 5, 6, 7, 8, 9, 10 or more), histidine tags (Hisn where n=3, 4, 5, 6, 7, 8, 9, 10 or more), linkers composed of glycine and serine residues, soluble polypeptide linkers (e.g., GST-GEKGKQ, SEQ ID NO:7), GSAT, SEG, and Z-EGFR linkers. Longer linkers, having a defined tertiary structure, can be used to facilitate display of a protein or peptide on ribosomes. Such linkers include, but are not limited to, fragments of gene III of filamentous phage M13mp192, a portion of the helical region of tolA, the extended region of tonB from E. coli, and a segment of protein D (pD) from the capsid of Lambda phage (see e.g., Yang et al. (2008) PLoS One 3(5):e2092; herein incorporated by reference). In addition, a linker domain comprising a small, computationally designed thermostable 3-helix bundle (SEQ ID NO:9) has been shown to facilitate display of an emerging protein on a stalled ribosome (see Example 1). Other suitable linker amino acid sequences will be apparent to those skilled in the art. (See e.g., Argos (1990) J. Mol. Biol. 211(4):943-958; Crasto et al. (2000) Protein Eng. 13:309-312; George et al. (2002) Protein Eng. 15:871-879; Arai et al. (2001) Protein Eng. 14:529-532; and the Registry of Standard Biological Parts (partsregistry.org/Protein_domains/Linker).

A plurality of proteins or peptides may be displayed simultaneously by this method. For example, this method can be used to display the collective proteins or peptides encoded by a genomic library for an organism or a cDNA library produced from RNA from an organism, or a selected subset of proteins or peptides of interest expressed by an organism, or engineered proteins or peptides. The DNA library used for display may be entirely or partially synthetic and may contain sequences optimized for the expression of a particular set of polypeptides. The plurality of DNA templates may be free in solution or immobilized on a solid support.

In one embodiment, a plurality of DNA templates is immobilized on a solid support. The solid support may comprise, for example, glass, quartz, silica, metal, ceramic, or plastic. Exemplary solid supports include a slide, a bead, a plate, a gel, a membrane, or the inner surface of a flow cell or microchannel. Each DNA template can be located at a known, predetermined position on the solid support such that the identity of each protein produced from the DNA template can be determined from its position on the solid support. Alternatively, DNA templates can be bound randomly to the support, wherein the identity of the protein produced from each DNA template can be determined by sequencing of the associated DNA template or characterization of the protein itself.

Nucleic acids can be coupled to a solid support by physical or chemical means using any method known in the art. A substrate may be added to the surface of a solid support to facilitate attachment of DNA templates. DNA array fabrication methods are well-known, and include various photochemistry-based methods, laser writing, electrospray deposition, inkjet and microjet deposition or spotting technologies, photolithographic oligonucleotide synthesis processes, as well as contact printing technologies, including contact pin printing and microstamping. The combination of suitable robotics, micromechanics-based systems, and microscopical techniques makes technically feasible the ordered deposition of up to millions of nucleic acids per cm2 on a solid support. See e.g., Rehman et al. (1999) Nucleic Acids Research 27:649-655; Heller et al. (2002) Annu. Rev. Biomed. Eng. 4:129-153; Dufva (2009) Methods Mol. Biol. 529:1-22; Sethi et al. (2008) Bioconjug Chem. 19(11):2136-2143; Adessi et al. (2000) Nucleic Acids Res. 28(20):E87; Okamoto et al. (2000) Nat. Biotechnol. 18(4):438-441; Barbulovic-Nad et al. (2006) Crit. Rev. Biotechnol. 26(4): 237-259; herein incorporated by reference.

In one embodiment, acrylamide-modified nucleic acids are immobilized on a solid support containing exposed acrylic groups (e.g., silanized glass or plastic). The acrylamide group can be added to a nucleic acid during oligonucleotide synthesis using an acrylamide phosphoramidite. The acrylamide modification copolymerizes with acrylamide monomers to allow formation of a stable polyacrylamide co-polymer containing the immobilized nucleic acid. A layer containing immobilized DNA can be fabricated on a support by polymerizing an acrylamide matrix on the surface of the support and adding acrylamide-modified nucleic acids. Polymerization is catalyzed using standard chemical or photochemical methods. See, e.g., Rehman et al. (1999) Nucleic Acids Research 27:649-655; herein incorporated by reference in its entirety.

A DNA template can be immobilized on a solid support by hybridization to a complementary capture oligonucleotide attached to the surface of the solid support. A capture oligonucleotide may have a unique sequence complementary to a single DNA template in a mixture of DNA templates to allow selective capture of a particular DNA template. Alternatively, a universal capture oligonucleotide may be used that binds to a complementary adapter sequence added to DNA templates to allow a single type of capture oligonucleotide to be used to capture multiple DNA templates on a solid support. DNA templates may be arranged randomly or ordered in an array on a solid support, wherein each DNA template occupies a discrete position on the solid support.

In one embodiment, the method further comprises amplification of at least one DNA template. Amplification may be performed using any known method, such as polymerase chain reaction (PCR) or other nucleic acid amplification process (e.g., ligase chain reaction (LGR), nucleic acid sequence-based amplification (NASBA), transcription-mediated amplification (TMA), Q-beta amplification, strand displacement amplification, or target mediated amplification). See, e.g., PCR Protocols, Vol. 226 (Methods in Molecular Biology, J. Bartlett and D. Stirling eds., Humana Press; 2nd edition, 2003; Wiedmann et al. (1994) PCR Methods Appl. 3(4):551-64; Deiman et al. (2002) Mol. Biotechnol. 20(2):163-179; Guatelli et al., Proc. Natl. Acad. Sci. USA (1990) 87:1874-1878 and J. Compton, Nature (1991) 350:91-92 (1991); Hill (2001) Expert Rev. Mol. Diagn. 1:445-455; WO 89/1050; WO 88/10315; EPO Publication No. 408,295; EPO Application No. 8811394-8.9; WO91/02818; U.S. Pat. Nos. 5,399,491, 6,686,156, and 5,556,771; Walker et al., Clin. Chem. (1996) 42:9-13 and EPA 684,31; herein incorporated by reference in their entireties. In particular, clonal amplification methods such as, but not limited to bridge amplification, emulsion PCR (ePCR), or rolling circle amplification may be used to cluster amplified nucleic acids in a discrete area (see, e.g., U.S. Pat. Nos. 7,790,418; 5,641,658; 7,264,934; 7,323,305; 8,293,502; 6,287,824; and International Application WO 1998/044151 A1; Lizardi et al. (1998) Nature Genetics 19: 225-232; Leamon et al. (2003) Electrophoresis 24: 3769-3777; Dressman et al. (2003) Proc. Natl. Acad. Sci. USA 100: 8817-8822; Tawfik et al. (1998) Nature Biotechnol. 16: 652-656; Nakano et al. (2003) J. Biotechnol. 102: 117-124; herein incorporated by reference). For this purpose, DNA templates may include adapter sequences (e.g., adapters with sequences complementary to universal amplification primers or bridge PCR amplification primers) at the 5' and 3' ends suitable for high-throughput amplification. For example, bridge PCR primers, attached to a solid support, can be used to capture DNA templates comprising adapter sequence complementary to the bridge PCR primers. The DNA templates can then be amplified, wherein the amplified products of each DNA template cluster in a discrete area on the solid support. In one embodiment, DNA templates are attached to a solid support, amplified, and sequenced prior to displaying ribosomal translation products for functional screening.

In another embodiment, the method further comprises sequencing at least one DNA template. Any sequencing method may be used, including, but not limited to Maxam-Gilbert sequencing, Sanger sequencing (i.e., chain-termination method), sequencing-by-synthesis (SBS), sequencing-by-ligation, pyrosequencing, ion torrent sequencing, and single-molecule real-time sequencing. In one embodiment, a plurality of DNA templates is sequenced by a high-throughput DNA sequencing method. See, e.g., Pettersson et al. (2009) Genomics 93 (2): 105-111; Maxam & Gilbert (1977) Proc. Natl. Acad. Sci. U.S.A. 74 (2): 560-564; Sanger et al. (1977) Proc. Natl. Acad. Sci. U.S.A. 74 (12): 5463-5467; Ronaghi et al. (1996) Analytical Biochemistry 242 (1): 84-89; Brenner et al. (2000) Nature Biotechnology 18 (6): 630-634; Schuster (2008) Nat. Methods 5 (1):16-18; Margulies et al. (2005) Nature 437: 376-380; Shendure et al. (2005) Science 309:1728-1732; Thompson et al. (2012) Electrophoresis 33(23):3429-3436; Merriman et al. (2012) Electrophoresis. 33(23):3397-3417; and Pareek et al. (2011) Journal of applied genetics 52 (4): 413-435).

The methods of the invention can be adapted to perform massively parallel high-throughput protein screening. For multiplex assays, DNA templates can be immobilized on a solid support, such as on beads within confined locations of a carrier (e.g. capillary), or on the inner surface of a microchannel or flow chamber, or on the surface of a microscope slide, or the like. The surface can be a planar surface, or a coated surface. Additionally, the surface may comprise a plurality of microfeatures arranged in spatially discrete regions to produce a texture on the surface, wherein the textured surface provides an increase in surface area as compared to a non-textured surface.

Arrays may comprise a plurality or library of displayed ribosomal translation products, such as antigens, antibodies, enzymes, substrates, receptors, or regulatory molecules. Such arrays can be used, for example, in high throughput genetic or pharmacological screening, epitope mapping, protein engineering, or proteomic profiling. For high-throughput screening, arrays are preferably contained within a flow cell or a microfluidic device. Tens of millions to billions of proteins, peptides, or ribosomally translated small molecules potentially can be quantitatively screened simultaneously. Functional screening can be performed in a continuous flow or a stop-flow system, wherein the proteins are displayed on immobilized DNA templates, as described herein, and different reagents and buffers are pumped into the system at one end and exit the system at the other end. Reagents and buffers may flow continuously or may be held in place for a certain period to allow ligand binding or enzymatic reactions to proceed. Additionally, ligands or substrates may be labeled to facilitate detection and quantitative analysis of binding interactions or enzymatic reactions.

In one embodiment, protein screening assays are performed in a high-throughput sequencer. Ribosomal translation products (e.g., proteins or peptides, biologically active fragments thereof, or other ribosomally translated molecules) can be displayed on DNA templates in a sequencer using the methods described herein, and then simultaneously characterized functionally directly on the sequencing flow cell. Hence, the methods of the invention offer significant added value to high-throughput sequencing instrumentation, allowing high-throughput sequencing to readily be combined with protein screening.

B. Applications

The methods of the present invention may be used in proteomic applications, including, but not limited to proteome-wide ligand screening, mapping proteins, such as protein contacts and biomolecular networks, identifying enzyme interactions with substrates or inhibitors, and identifying receptor interactions with hormones, agonists or antagonists. For example, the methods of the invention can be used to detect particular interactions and activities, including but not limited to protein-protein, protein-lipid, protein-antibody, protein-small molecule, protein-DNA, protein-RNA, protein-receptor, protein virus, lectin-glycan, and lectin-cell interactions, and to identify substrates or enzymes involved in various cellular reactions, including phosphorylation, ubiquitylation, acetylation, methylation, and nitrosylation, as well as to profile immune responses. See Kodadek (2001) Chem. Biol. 8(2):105-115; Cretich et al. (2006) Biomol. Eng. 23(2-3):77-88; Zhu et al. (2012) Adv. Genet. 79:123-155; which are herein incorporated by reference.

In certain embodiments, the methods of the invention are used to display libraries of ribosomal translation products (e.g., proteins or peptides, biologically active fragments thereof, or other ribosomally translated molecules) for screening for biological activity. A plurality of ribosomal translation products is displayed on the DNA templates encoding them as described herein. The ribosomal translation products are contacted with a target molecule of interest and assayed for biological activity in the presence of the target molecule in order to identify displayed molecules that have biological activity. For this purpose, the DNA templates displaying the ribosomal translation products may be free in solution or immobilized on a solid support. If displayed on a solid support, the ribosomal translation products may have discrete addressable positions in an ordered array to allow ready identification of the ribosomal translation products showing biological activity with a particular agent. Alternatively, the DNA templates displaying the ribosomal translation products may be distributed randomly on a solid support and indexed based on sequencing the DNA templates. Biological activities that may be assayed include enzymatic activity, substrate activity, ligand-binding activity, agonist activity, antagonist activity, transport activity, or any other biological activity. Any target molecule can be chosen for study, including, but not limited to, a receptor, a ligand, an antibody, an antigen, an enzyme, a transporter, a substrate, an inhibitor, an activator, a cofactor, a drug, a nucleic acid, a lipid, a carbohydrate, a glycoprotein, an extracellular matrix component, a small organic molecule, or an inorganic molecule.

The target molecule may comprise a detectable label in order to facilitate detection of binding of the target molecule to displayed proteins or peptides or other ribosomally translated molecules. Detectable labels suitable for use in the present invention include any composition detectable by spectroscopic, photochemical, biochemical, immunochemical, electrical, optical, or chemical means. Useful labels in the present invention include biotin or other streptavidin-binding proteins for staining with labeled streptavidin conjugates, magnetic beads (e.g., DYNABEADS® magnetic beads), fluorescent dyes (e.g., phycoerythrin, YPet, fluorescein, TagRFP, Texas red, rhodamine, green fluorescent protein, and the like, see, e.g., Molecular Probes, Eugene, Oreg., USA), quantum dots, radiolabels (e.g., 3H, 125I, 35S, 14C, or 32P), enzymes (e.g., horseradish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; 4,366,241; 7,416,854; 8,114,681; 7,229,769; 6,846,645; 7,232,659; 6,872,578; 7,897,257; 6,730,521; 5,972,721; 7,498,177; 7,235,361; and 6,306,610; herein incorporated by reference.

In one embodiment, a protein or peptide library displayed according to the methods of the invention is used for the identification of substrates for an enzyme, such as, but not limited to a protease, a kinase, a phosphatase, an acetyltransferase, a methyltransferase, a deacetylase, a peptidylarginine deiminase, and a protein ligase. For example, a DNA library encoding protein or peptide substrates is created using methods known in the art. The substrates are displayed on the DNA templates encoding them according to the methods of the invention. The substrate library may be constructed such that a label (e.g., radioisotope, fluorophore or other chromophore) or an affinity tag is fused to the displayed proteins or peptides to allow detection of enzyme activity. For example, protease activity may be detected by loss of a label upon cleavage of a peptide substrate. Addition or loss of a transferred group (e.g., phosphoryl, methyl, acetyl, imino, or amino group) may be detected by labeling the transferred moiety. Any suitable method for assaying enzyme activity may be used, and methods of assaying such enzymes are well known in the art. See, e.g., Zhu et al. (2012) Adv. Genet. 79:123-155; Kim et al. (2010) Biopolymers 94(6):753-762; Lin et al. (2010) Brief Funct Genomics 9(1):32-42; Fan et al. (2007) Assay Drug Dev. Technol. 5(1):127-136; Goddard et al. (2004) Curr Opin Biotechnol. 15(4):314-322; herein incorporated by reference.

In another embodiment, the invention includes a method of screening a library of ribosomal translation products (e.g., proteins or peptides, biologically active fragments thereof, or other ribosomally translated molecules) for the ability to bind to a target molecule, the method comprising: a) providing a plurality of DNA templates collectively encoding the library of ribosomal translation products; b) displaying each ribosomal translation product according to a method described herein; c) contacting the plurality of ribosomal translation products with the target molecule; and d) identifying at least one displayed ribosomal translation product that binds to the target molecule. The target molecule may comprise a detectable label to allow detection of binding of the target molecule to at least one displayed ribosomal translation product. Binding of a target molecule to a displayed ribosomal translation product may further be characterized quantitatively. The method may further comprise enriching the DNA library for DNA templates encoding ribosomal translation products that bind to the target molecule, or depleting the DNA library of DNA templates encoding ribosomal translation products that do not bind to the target molecule or that have undesired activities.

The methods of the invention can also be used for mapping protein epitopes, including multiplex mapping, and detecting an immune response to target antigens. In one embodiment, the invention includes a method of performing epitope mapping, the method comprising: a) providing a plurality of DNA templates encoding peptide fragments of a protein; b) displaying the peptide fragments according to the methods described herein; and c) detecting binding of an antibody to at least one peptide fragment in order to identify an epitope of the protein that binds to the antibody.

In another embodiment, the invention includes a method of profiling an immune response of a subject, the method comprising: a) providing a plurality of DNA templates each encoding a different target antigen of interest; displaying each target antigen according to the methods described herein; b) obtaining a biological sample (e.g., blood) from the subject; and c) detecting binding of at least one antibody or lymphocyte from the biological sample to at least one target antigen of interest. A humoral or cellular immune response may be profiled by this method. For example, binding of one or more antibodies (e.g., autoantibodies or antibodies to a particular antigen or set of antigens), T cells, or B cells produced by an immune response can be detected.

In another embodiment, the invention includes a medical diagnostic instrument that can characterize a given patient's serum antibody repertoire against one or more infectious agents (e.g., bacteria or viruses) wherein the diagnostic instrument displays a panel of epitopes derived from the one or more infectious agents capable of binding to reactive antibodies. Such an instrument can be used to determine if a patient has ever contracted, has been effectively immunized against, or is currently in later stages of infection with an infectious agent represented by the displayed epitopes in the panel.

In one embodiment, the diagnostic instrument displays millions to billions of viral protein epitopes. Such an instrument can be used to determine if a patient has ever contracted, has been effectively immunized against, or is currently in later stages of infection with the viruses represented in the panel. Comprehensive characterization of a patient's immune complement against particular viruses will provide unprecedented insight into exactly how an individual's immune system recognizes the pathogen's proteome. Such an instrument will provide a revolutionary tool in diagnosing, tracking, and predicting susceptibility to viral infections, ranging from the current year's strains of the flu to rare viral diseases. The extremely detailed, strain-specific data about a patient's immunological memory generated by this instrument will enable rapid and precise development of synthetic vaccines based on targeted epitopes, and inform predictive models of patient outcome to future viral exposure.

The methods of the invention also will find use in protein engineering. Many engineered proteins are developed for use as therapeutics, diagnostics, sensors, and scientific and industrial reagents. For each protein there are practically unlimited combinations of sequence mutations that can alter enzymatic activity, binding affinity and specificity, thermal or chemical stability, shelf life, immunogenicity, or pharmacokinetics. The development cycle of each engineered protein involves selecting sequence variants with directed evolution or rationally predicting mutations that will change function in desired ways. Then, selected individual candidate proteins must be expressed and characterized to identify those with the desired properties. Conventional methods of expressing and characterizing large numbers of proteins are laborious. Thus, the methods of the current invention provide an enormous advantage by enabling millions to billions of selected or rationally designed candidate proteins to be screened simultaneously.

For example, the present invention may be broadly applied to directed evolution methods to isolate, enhance or otherwise alter, peptide and polypeptide sequences that perform useful or desired functions including binding, catalysis, assembly, transport, and the like. These methods may be used, for example, to optimize enzymes, vaccines, or therapeutics and to discover and develop proteins or peptides with novel properties, such as peptide molecular transformation catalysts, whole-cell reagents, peptides that promote self-assembly, in vivo targeting peptides for drug and gene delivery, peptides that bind to material surfaces, e.g., semiconductors, inhibitors of bacterial or viral pathogenesis, peptides that mediate endocytosis and cellular entry, peptide mimics of non-peptide ligands, and peptides for bioremediation. See Georgiou, G., et al. (1997) Nat. Biotechnol. 15(1):29-34; Pasqualini, R. and E. Ruoslahti (1996) Nature 380(6572):364-366; Whaley, S. R., et al. (2000) Nature 405(6787):665-668; Fields, S, and R. Sternglanz (1994) Trends in Genetics 10(8):286-292; Kim, W. C., et al. (2000) J. Biomol. Screen. 5(6):435-440; Yang, W. P., et al. (1995) J. Mol. Biol. 254(3): 392-403; Poul, M. A., et al. (2000) J. Mol. Biol. 301(5):1149-1161; James, L. C., et al. (2003) Science 299(5611):1362-1367; Feldhaus, M. J., et al. (2003) Nat. Biotechnol. 21(2):163-170; Kjaergaard, K., et al. (2001) Appl. Environ. Microbiol. 67(12):5467-5473, and Shusta, E. V., et al. (1999) Curr. Opin. Biotechnol. 10(2): 117-122, which are herein incorporated by reference in their entireties.

A library of gene variants may be created, for example, using error-prone PCR or DNA shuffling. The library of gene variants may be used to display a plurality of protein variants according to the methods described herein. The protein variants can then be assayed for the desired biological activity. Methods for selecting or screening protein variants for desired biological activities are well known and can be used to identify and isolate protein variants with desired functions. The sequences of DNA templates encoding protein variants having the desired biological activity may be sequenced and/or further mutated to further improve the properties of the protein variants. Multiple rounds of mutagenesis and selection may be used to optimize function and enrich a DNA library for DNA templates encoding protein variants with desired biological activities. In one embodiment, the method further comprises depleting the library of DNA templates encoding protein variants with undesired activities. See, e.g., McCullum et al. (2010) Methods Biol. 634:103-109; Labrou (2010) Curr. Protein Pept. Sci. 11(1): 91-100; Fox et al. (2008) Trends Biotechnol. 26(3):132-138; Yuan et al. (2005) Microbiol. Mol. Biol. Rev. 69(3):373-392; herein incorporated by reference in their entireties.

The methods of the invention will also find use in the field of functional genomics. With the advent of high-throughput sequencing, millions of disease-associated mutations have been identified in protein coding regions. Each nonsynonymous mutant gene produces a distinct protein variant. The vast majority of these mutant proteins do not behave pathologically in their physiological context, i.e., many mutations are correlated with, but not causative of disease. Individually characterizing many millions of mutant proteins to identify the handful of mutant proteins that effect particular disease mechanisms (e.g. abrogate particular critical protein-protein interactions) is essential to understanding disease pathways and developing effective therapeutic strategies. However, functional characterization of each distinct mutant is unrealistic with current methods due to the time-consuming, low through-put methods required. The ability to perform widespread protein screening by the methods of the invention would enable comprehensive quantitative binding assays to be simultaneously performed with all point mutants, all double mutants, and, depending on length, perhaps all triple mutants of a physiologically relevant protein of interest.

Protein arrays, generated using the methods of the invention, can be specifically designed for various purposes. In many applications, the immobilized protein array itself may be the ultimate invention. By enabling a huge number of protein receptors with diverse molecular specificities to be immobilized on a chip and reading out individual binding events (e.g. via fluorescence), the array will effectively be a huge multisensor that could function analogously to the animal olfactory and taste systems. Protein arrays have the potential to perform with unprecedented specificity in applications as broad as detecting subtle disease markers in a diagnostic setting, detecting trace explosives in an airport, or determining environmental contamination levels.

C. Kits

Reagents for displaying ribosomal translation products, as described herein, can be provided in kits with suitable instructions. The kit may further comprise other necessary reagents for preparing arrays or using them, as described above. The reagents for displaying a ribosomal translation product (e.g., nucleic acids and reagents for RNA transcription and in vitro translation) and for preparing an array (e.g., a solid support, adapters, and capture oligonucleotides or bridge PCR primers) may be contained in separate containers. Additionally, instructions (e.g., written, tape, VCR, CD-ROM, DVD, flash drive, Blu-ray, etc.) for preparing or using arrays comprising a plurality of ribosomal translation products (e.g., proteins or peptides, fragments thereof, or other ribosomally translated molecules) may be included in the kit. The kit may also contain other packaged reagents and materials (e.g., buffers, enzymes, nucleotides, primers and other reagents for sequencing or PCR, and the like).

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

On Chip In Situ Production of an Ultra High-Throughput Protein Array

We have previously shown that we can display a polypeptide on its DNA template with modified in vitro transcription and translation methods using a molecular roadblock at the 3'-end of the sense strand (or 5'-end of the antisense strand) of the DNA. See U.S. Pat. No. 10,011,830; herein incorporated by reference in its entirety. When an $E.$ $coli$ RNA polymerase (RNAP) reaches the roadblock (e.g. a streptavidin bound to a covalently linked biotin on the DNA template), it stalls, displaying the RNA. When a ribosome initiates on the displayed RNA and reaches the stalled polymerase, now itself a roadblock, its progression halts and the nascent peptide it produced is stably displayed.

Many potential applications of this technology relate to the ability to display proteins and peptides on chip. Here, we describe the various changes, optimizations, and innovations we have made to allow the display of both short peptides and full-length proteins on a sequencing chip. Many changes have been made to the DNA library constructs and experimental protocols described previously in order to display proteins and peptides on chip.

Translation-Only In Vitro Translation Mix

In both the previous and current versions of our peptide display methods the PUREXPRESS® in vitro translation system was used. However, the current version uses a custom-formulated translation-only (i.e. transcription machinery omitted) mix. PUREXPRESS® cell-free translation system is a commercially-available in vitro translation system sold by New England Biolabs (NEB). The system is based on $E.$ $coli$ (prokaryotic) translation machinery. Instead of relying on cell extract, PUREXPRESS® cell-free translation system is entirely reconstituted from purified components. This provides the unique advantage of enabling custom formulations of the system that leave out certain components. It should be noted that, in addition to the standard kit with all components, NEB already sells in their standard catalog a few kits which leave out various combinations of components (NEB, Cell-Free Expression. neb-.com/products/protein-expression-and-purification-technologies/cell-free-expression, 2017). With NEB's cooperation, we were able to obtain a new custom formulation, not available as a standard commercial product, which is specific to our application. The custom PUREXPRESS® cell-free translation system formulation was specified by us, but produced by NEB.

Our custom formulation omits the transcription machinery, as well as all three release factors. In all standard PUREXPRESS® cell-free translation system formulations, T7 RNAP and high concentrations of all 4 NTPs are present to enable protein expression directly from DNA template. In our methods on chip, the translation mix is added after mRNA has been produced and displayed by the $E.$ $coli$ RNAP that is stalled at the streptavidin roadblock. In order to prevent any disruption that the T7 RNAP or NTPs might cause to the stalled $E.$ $coli$ RNAP, we omitted T7 RNAP, CTP, and UTP, as described below. Components present in the standard formulation but omitted in ours are designated with a Δ.

Our custom ΔT7 RNAP, ΔCTP, ΔUTP, ΔRF123 PUREXPRESS® cell-free translation system features:
Transcription machinery omitted
    ΔT7 RNAP
    ΔCTP
    ΔUTP
    (note that ATP and GTP are still present, as they are necessary components of the energy regeneration system)
Release factors omitted:
    ΔRF1 (prevents ribosome release at the Amber codon, as described in the stall sequence section below)
    ΔRF2
    ΔRF3
Note that elongation factor P (EF-P) is not present in any PUREXPRESS® cell-free translation system formulation, which allows stalling at polyproline stretches, as described in the stall sequence section below.

The custom formulation has been shown to be necessary for protein display on chip to work, when compared with the standard ΔRF123 mix.

Stall Sequence

Instead of relying on a physical molecular roadblock to halt the progression of the translating ribosome, ribosomal stalling is now induced at a stall sequence. The stall sequence is a sequence internal to the RNA transcript that induces ribosomal stalling. It is located after the open reading frame that encodes the protein or peptide sequence of interest such that when the ribosome stalls that peptide sequence has already been translated and is stably displayed.

Some sequences have been discovered to exist in nature that stall ribosomal progression when translated (e.g. TnaC, SecM (Vazquez-Laslop et al. (2008) Molecular Cell 30(2): 190-202, Muto et al. (2006) Molecular Cell 22(4):545-552). It has been shown that these can be used for Ribosome Display and could, in principle, be candidates for use in this application. Instead, however, I rationally designed the stall sequence that we used for maximum stalling potential, as described below. Internally, I have called this designed stall sequence CJL-PPP. This sequence appears to result in higher stalling efficiency than SecM or TnaC. Features of the stall sequence include:

Translated amino acid sequence:

(SEQ ID NO: 11)
KEAAAKFSTKWWIIDKWRHRPPP(Am)RLT

Length 27 aa (81 nt)
Am indicates the "Amber" stop codon, TAG
  RF1 normally mediates release of the ribosome from the RNA transcript at an amber codon, but it has been omitted from our translation mix
DNA sequence used in our implementation:

(SEQ ID NO: 12)
AAAGAAGCAGCTGCAAAGTTCAGCACGAAATGGTGGATAATTGACAAATG
GCGCCACCGTCCGCCACCTTAGCGCCTCACC

The rational design process of this sequence was largely based on 3 principles:
E. coli ribosomes stall at polyproline-coding sequences in the absence of EF-P (Starosta et al. (2014) Nucleic Acids Research 42(16):10711-10719, Ude et al. (2013) Science 339(6115):82-85)
  Triple proline immediately precedes the amber codon
  The context amino acids that immediately precede the triple-proline motif greatly affect stalling. Near-maximally-stalling residues "RHR" were chosen
Transplantation of critical amino acids from both the SecM and TnaC sequences (dark gray) that are thought to interact with the ribosomal exit tunnel.
  Light gray residues are transplanted critical residues. See Table below:

Inclusion of the Amber stop codon with RF1 omitted from the in vitro translation mix.

The stall sequence is needed for efficient display on chip (see FIG. 4).

Construct Structure

A schematic of the functional construct is shown in FIG. 5. In addition to the introduction of the ribosome stall sequence, other elements of the construct have been updated as outlined here for completeness:

The construct contains sequences that are essentially the same as described in Example 1.
  Sequencing adapters (C and D') on each terminus, enabling the construct to be bridge-amplified into clusters on the Illumina platform.
  Initial stall sequence to capture one E. coli RNA polymerase per construct under depleted nucleotide conditions.
    Same sequence used in RNA-MaP (Buenrostro et al. (2014) Nat. Biotech. 32(6):562-568; herein incorporated by reference in its entirety) also from our lab.
This construct contains sequences that are categorically similar, but have been optimized for better performance.
  We use the full length E. coli promoter sequences (from GenBank X73047.1) instead of the shorter, incomplete promoter used previously.
  Sequence:

(SEQ ID NO: 13)
TATCAAAAAGAGTATTGACTTAAAGTCTAACCTATAGGATACTTACAGCC

We use an optimized Shine Dalgarno sequence in an empirically optimized, efficient context for ribosomal initiation.
  Sequence:

(SEQ ID NO: 14)
AGAAATAATTTTGTTTAACTTTAAGAAGGAGATATACAT

This construct is the product of many generations of testing different potential display mechanisms and contains vestigial sequences that may not participate significantly in the current functionality.
  The terB site is a high-affinity recognition site for the protein Tus. Though Tus can be used as a molecular roadblock (Tome et al. (2014) Nature Methods 11(6): 683-688), we do not introduce it in our methods, so the sequence is presumably inert.
  The 2Xybbr peptide is a substrate for SFP labeling with CoA conjugates (Yin et al. (2005) Proceedings of the National Academy of Sciences of the United States of America 102(44):15815-15820). We do not use SFP or any CoA conjugates in our methods, so the

| SecM (SEQ ID NO: 15) | F | T | P | Q | A | K | F | S | T | P | V | W | I | S | Q | A | Q | G | I | R | A | G | P | Q | R | L | T |
| --- | --- | --- | --- | --- | --- | --- | --- | --- | --- | --- | --- | --- | --- | --- | --- | --- | --- | --- | --- | --- | --- | --- | --- | --- | --- | --- | --- |
| TnaC (SEQ ID NO: 16) | N | I | L | H | I | C | V | T | S | K | W | F | N | I | D | N | K | I | V | D | H | R | P | Am | F | A | L |
| CJL-PPP (SEQ ID NO: 17) | K | E | A | A | A | K | F | S | T | K | W | W | I | D | K | W | R | H | R | P | P | P | Am | F | A | L | peptide is probably inert from the perspective of enzymatic reactivity. It now plays a role as a spacer peptide.

Using the above DNA library constructs, reagents, and methods we are able to definitively show stable display of the following polypeptides on a MiSeq sequencing chip:

a library of mutants of the short 8-amino acid FLAG® tag peptide a mutational scan of an 180-amino acid full-length enzyme (SNAP-tag, an evolved $O^6$-alkylguanine-DNA alkyltransferase (Gronemeyer et al. (2006) Protein Engineering, Design and Selection 19(7):309-316))

In both experiments, the constructs were first sequenced on a MiSeq. Then the sequenced flow cell was moved to our custom imaging station and RNA was generated with a similar protocol to RNA-MaP (Buenrostro et al. (2014) Nat. Biotech 32(6):562-568). Our custom translation-only PUR-EXPRESS® cell-free translation system formulation was then introduced into the chip for 1 hour at 37° C. to generate peptides.

FLAG Peptide On-Chip Antibody Binding

For the FLAG® tag experiments, the displayed peptide was first incubated with mouse monoclonal M2 anti-FLAG® tag antibody, then probed with fluorescently labeled goat anti-mouse secondary antibody. Imaging the chip before and after antibody binding demonstrates that peptide is present on the chip and recognized by the antibody (FIG. 6).

A later experiment, which quantified the fluorescence-per-cluster of those images as increasing concentrations of M2 anti-FLAG® tag antibody were introduced, allowed us to calculate an antibody titer for each mutant FLAG® tag epitope target. The resulting pattern agrees well with the expected literature motif (Srila and Yamabhai (2013) Applied Biochemistry and Biotechnology 171(3):583-589) for M2 anti-FLAG® tag target peptide specificity, further validating the method (FIG. 7).

SNAP-Tag On-Chip Full-Length Protein Functional Study

In the SNAP-tag® human O6-alkylguanine-DNA-alkyltransferase variant tag experiment, after generation of a library of SNAP-tag® human O6-alkylguanine-DNA-alkyltransferase variant tag and a large library of mutational variant proteins of the same size on-chip, 1 µM SNAP-Surface 549® red fluorescent substrate (a fluorescent substrate for SNAP-tag® human O6-alkylguanine-DNA-alkyltransferase variant tag) was introduced. SNAP-tag® human O6-alkylguanine-DNA-alkyltransferase variant tag is an enzyme that, when active, catalyzes self-labeling with the fluorescent substrate. Quantification of fluorescence of clusters encoding SNAP-tag® human O6-alkylguanine-DNA-alkyltransferase variant tag over time showed activity demonstrating that the full-length protein is stably displayed and functional (FIG. 8).

While the preferred embodiments of the invention have been illustrated and described, it will be appreciated that various changes can be made therein without departing from the spirit and scope of the invention.

What is claimed is:

1. A method for displaying a polypeptide on a double-stranded DNA template encoding it, the method comprising:
   a) providing a double stranded DNA template that encodes the polypeptide, wherein the DNA template comprises:
      i) a promoter operably linked to an open reading frame (ORF);
      ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template anti sense strand and the 3' end of the DNA template sense strand; and
      iii) a nucleic acid encoding a ribosome stall sequence, wherein the nucleic acid encoding the ribosome stall sequence is located on the 3' side of the ORF, wherein the ribosome stall sequence comprises:
         a polyproline-coding sequence adjacent to a stop codon, wherein the polyproline-coding sequence is located on the 5' side of the stop codon, and
         an arginine-histidine-arginine coding sequence adjacent to the polyproline-coding sequence, wherein the arginine-histidine-arginine coding sequence is located on the 5' side of the polyproline-coding sequence;
   b) adding an RNA polymerase that can be blocked by the molecular roadblock, wherein the RNA polymerase binds to the promoter of the DNA template and carries out transcription of the DNA template until the RNA polymerase stalls at the molecular roadblock where the RNA polymerase is blocked from further progress, such that the DNA template and transcribed mRNA remain associated; and
   c) adding a ribosome that binds to a ribosomal binding site on the mRNA, wherein the ribosome carries out protein translation until the ribosome reaches the ribosome stall sequence, wherein the ribosome is blocked from further progress, such that the ribosome displays the nascent polypeptide while remaining associated with the mRNA.

2. The method of claim 1, wherein the stop codon is an amber stop codon.

3. The method of claim 1, wherein the stop codon is an ochre or opal stop codon.

4. The method of claim 1, wherein the polyproline-coding sequence is a coding sequence for a triple-proline motif.

5. The method of claim 1, wherein:
   a) the ribosome stall sequence comprises a coding sequence for a polypeptide comprising:
      i) an amino acid sequence selected from the group consisting of SEQ ID NO: 11 and SEQ ID NO:17; or
      ii) an amino acid sequence having at least 95% sequence identity to a sequence selected from the group consisting of SEQ ID NO: 11 and SEQ ID NO:17, wherein the ribosome stalls at the ribosome stall sequence; or
   b) the nucleic acid encoding the ribosome stall sequence comprises:
      i) the nucleotide sequence of SEQ ID NO: 12; or
      ii) a nucleotide sequence having at least 95% sequence identity to the nucleotide sequence of SEQ ID NO: 12, wherein the ribosome stalls at the encoded ribosome stall sequence on the transcribed mRNA.

6. The method of claim 1, wherein protein translation is carried out using an in vitro cell-free expression system lacking one or more release factors, such that the ribosome is not released from the stop codon on the mRNA.

7. The method of claim 6, wherein:
   i) the protein translation is carried out using an in vitro cell-free expression system lacking any release factors;
   ii) codon usage in the ORF is optimized for expression in the cell-free expression system;
   iii) the one or more release factors are selected from the group consisting of release factor 1 (RFI), release factor 2 (RF2), and release factor 3 (RF3); or
   iv) one or more non-canonical amino acids are incorporated into the polypeptide.

8. The method of claim 6, wherein the stop codon is the amber stop codon and protein translation is carried out using the in vitro cell-free expression system lacking the release factor 1 (RF1).

9. The method of claim 1, wherein;
   a) the DNA template is genomic DNA or cDNA;
   b) the molecular roadblock comprises a biotin-streptavidin complex;
   c) the ORF further comprises a sequence encoding a polypeptide linker;
   d) the promoter comprises the sequence of SEQ ID NO:13 or a sequence having at least 95% sequence identity to the sequence of SEQ ID NO:13;
   e) the ribosomal binding site comprises a Shine Dalgarno sequence; and/or
   f) the DNA template comprises one or more spacer sequences.

10. The method of claim 9, wherein the Shine Dalgarno sequence comprises the sequence of SEQ ID NO:14, or a sequence having at least 95% sequence identity to the sequence of SEQ ID NO:14, wherein the ribosome binds at the ribosomal binding site.

11. The method of claim 1, further comprising:
   cleaving the single-stranded mRNA proximal to the ribosome after the ribosome reaches the molecular roadblock;
   providing conditions that allow only one RNA polymerase to initiate transcription on the DNA template; and/or
   providing conditions that allow only one ribosome to initiate translation on the RNA transcript.

12. The method of claim 11, wherein the DNA template further comprises a polymerase stall sequence, wherein the first RNA polymerase to initiate transcription stalls at the stall sequence on the DNA template such that initiation of any other polymerase is blocked.

13. The method of claim 12, wherein the polymerase stall sequence comprises the sequence of SEQ ID NO:4, or a sequence having at least 95% sequence identity to the sequence of SEQ ID NO:4, wherein the RNA polymerase stalls at the polymerase stall sequence.

14. The method of claim 11, further comprising:
a) carrying out transcription under conditions of nucleotide starvation, wherein the RNA polymerase stalls at a particular position on the DNA template because the nucleotide needed for addition at that position is not provided;
b) removing or inactivating any unbound polymerases; and then
c) adding the missing nucleotide needed to resume transcription, which continues until the one bound RNA polymerase stalls at the molecular roadblock.

15. The method of claim 11, further comprising:
a) carrying out translation under conditions of amino acid starvation, wherein the ribosome stalls at a particular position on the RNA transcript because the amino acid needed for addition at that position is not provided;
b) removing any unbound ribosomes; and then
c) adding the missing amino acid needed to resume translation, which continues until the one bound ribosome reaches the ribosome stall sequence.

16. A method for displaying a plurality of polypeptides, the method comprising:
a) providing a plurality of double-stranded DNA templates encoding a plurality of polypeptides, wherein each DNA template comprises:
i) a promoter operably linked to an open reading frame (ORF);
ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template anti sense strand and the 3' end of the DNA template sense strand; and
iii) a nucleic acid encoding a ribosome stall sequence, wherein the nucleic acid encoding the ribosome stall sequence is located on the 3' side of the ORF, wherein the ribosome stall sequence comprises:
a polyproline-coding sequence adjacent to a stop codon, wherein the polyproline-coding sequence is located on the 5' side of the stop codon, and an arginine-histidine-arginine coding sequence adjacent to the polyprolinecoding sequence, wherein the arginine-histidine-arginine coding sequence is located on the 5' side of the polyproline-coding sequence; and
b) displaying a polypeptide on each DNA template according to the method of claim 1.

17. The method of claim 16, wherein:
the plurality of DNA templates comprises a genomic library or a cDNA library for an organism; or
the plurality of displayed polypeptides comprises a library of antigens, antibodies, enzymes, substrates, or receptors.

18. The method of claim 16, further comprising amplification of at least one DNA template.

19. The method of claim 16, wherein:
a) each DNA template further comprises a pair of adapter sequences at the ends of the DNA template to allow high-throughput sequencing or amplification of multiple DNA templates simultaneously by the same set of primers; or
b) the plurality of DNA templates is free in solution or immobilized on a solid support.

20. The method of claim 19, wherein the DNA templates are distributed randomly on the solid support or are ordered in an array on the solid support.

21. A protein array on a solid support produced by the method of claim 20, wherein a polypeptide is displayed on each DNA template on the solid support.

22. The protein array of claim 21, wherein:
a) the ribosome stall sequence comprises a coding sequence for a polypeptide comprising:
i) an amino acid sequence selected from the group consisting of SEQ ID NO: 11 and SEQ ID NO:17; or
ii) an amino acid sequence having at least 95% sequence identity to a sequence selected from the group consisting of SEQ ID NO: 11 and SEQ ID NO:17, wherein the ribosome stalls at the ribosome stall sequence;
b) the nucleic acid encoding the ribosome stall sequence comprises:
i) the nucleotide sequence of SEQ ID NO: 12; or
ii) a nucleotide sequence having at least 95% sequence identity to the nucleotide sequence of SEQ ID NO: 12, wherein the ribosome stalls at the encoded ribosome stall sequence on the transcribed mRNA;
c) the plurality of displayed polypeptides comprises a library of antigens, antibodies, enzymes, substrates, or receptors; or
d) the plurality of displayed polypeptides comprises a library of viral protein epitopes for one or more viruses.

23. A flow cell or a microfluidic device comprising the protein array of claim 21.

24. A method of performing epitope mapping, the method comprising:
a) providing a plurality of double stranded DNA templates encoding peptide fragments of a protein;
b) displaying the peptide fragments according to the method of claim 1, wherein each double stranded DNA template comprises:
i) a promoter operably linked to an open reading frame (ORF);
ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template antisense strand and the 3' end of the DNA template sense strand; and
iii) a nucleic acid encoding a ribosome stall sequence, wherein the nucleic acid encoding the ribosome stall sequence is located on the 3' side of the ORF, wherein the ribosome stall sequence comprises:
a polyproline-coding sequence adjacent to a stop codon, wherein the polyproline-coding sequence is located on the 5' side of the stop codon, and
an arginine-histidine-arginine coding sequence adjacent to the polyproline-coding sequence, wherein the arginine-histidine-arginine coding sequence is located on the 5' side of the polyproline-coding sequence; and c) detecting binding of an antibody to at least one displayed peptide fragment in order to identify an epitope of the protein that binds to the antibody.

25. A method of profiling an immune response of a subject, the method comprising:
   a) providing a plurality of double stranded DNA templates each encoding a different target antigen of interest;
   b) displaying each target antigen according to the method of claim 1, wherein each double stranded DNA template comprises:
      i) a promoter operably linked to a target antigen-encoding open reading frame (ORF);
      ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template antisense strand and the 3' end of the DNA template sense strand; and
      iii) a nucleic acid encoding a ribosome stall sequence, wherein the nucleic acid encoding the ribosome stall sequence is located on the 3' side of the ORF, wherein the ribosome stall sequence comprises:
         a polyproline-coding sequence adjacent to a stop codon, wherein the polyproline-coding sequence is located on the 5' side of the stop codon, and
         an arginine-histidine-arginine coding sequence adjacent to the polyproline-coding sequence, wherein the arginine-histidine-arginine coding sequence is located on the 5' side of the polyproline-coding sequence;
   c) obtaining a biological sample from the subject; and
   d) detecting binding of at least one antibody or lymphocyte from the biological sample to at least one displayed target antigen of interest.

26. The method of claim 25 comprising detecting one or more antibodies, T cells, or B cells produced by an immune response.

27. A method of screening a library of polypeptides for the ability to bind a target molecule, the method comprising:
   a) providing a plurality of double stranded DNA templates collectively encoding the library of polypeptides;
   b) displaying each polypeptide according to the method of claim 1, wherein each double stranded DNA template comprises:
      i) a promoter operably linked to an open reading frame (ORF) encoding a polypeptide of said library;
      ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template antisense strand and the 3' end of the DNA template sense strand; and
      iii) a nucleic acid encoding a ribosome stall sequence, wherein the nucleic acid encoding the ribosome stall sequence is located on the 3' side of the ORF, wherein the ribosome stall sequence comprises:
         a polyproline-coding sequence adjacent to a stop codon, wherein the polyproline-coding sequence is located on the 5' side of the stop codon, and
         an arginine-histidine-arginine coding sequence adjacent to the polyproline-coding sequence, wherein the arginine-histidine-arginine coding sequence is located on the 5' side of the polyproline-coding sequence;
   c) contacting the plurality of polypeptides with the target molecule; and
   d) identifying at least one displayed polypeptide that binds to the target molecule.

28. A method of screening a library of polypeptides for biological activity in the presence of a target molecule, the method comprising:
   a) providing a plurality of double stranded DNA templates collectively encoding the library of polypeptides;
   b) displaying each polypeptide according to the method of claim 1, wherein each double stranded DNA template comprises:
      i) a promoter operably linked to an open reading frame (ORF) encoding a polypeptide of said library;
      ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template antisense strand and the 3' end of the DNA template sense strand; and
      iii) a nucleic acid encoding a ribosome stall sequence, wherein the nucleic acid encoding the ribosome stall sequence is located on the 3' side of the ORF, wherein the ribosome stall sequence comprises:
         a polyproline-coding sequence adjacent to a stop codon, wherein the polyproline-coding sequence is located on the 5' side of the stop codon, and
         an arginine-histidine-arginine coding sequence adjacent to the polyproline-coding sequence, wherein the arginine-histidine-arginine coding sequence is located on the 5' side of the polyproline-coding sequence;
   c) contacting the plurality of polypeptides with the target molecule;
   d) assaying for biological activity in the presence of the target molecule; and
   e) identifying at least one displayed polypeptide that has biological activity.

29. A method of screening a plurality of protein variants for a biological activity, the method comprising:
   a) providing a plurality of double stranded DNA templates comprising a library of gene variants encoding a plurality of protein variants;
   b) displaying the plurality of protein variants according to the method of claim 1, wherein each double stranded DNA template comprises:
      i) a promoter operably linked to an open reading frame (ORF) encoding a protein variant of said library;
      ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template antisense strand and the 3' end of the DNA template sense strand; and
      iii) a nucleic acid encoding a ribosome stall sequence, wherein the nucleic acid encoding the ribosome stall sequence is located on the 3' side of the ORF, wherein the ribosome stall sequence comprises:
         a polyproline-coding sequence adjacent to a stop codon, wherein the polyproline-coding sequence is located on the 5' side of the stop codon, and
         an arginine-histidine-arginine coding sequence adjacent to the polyproline-coding sequence, wherein the arginine-histidine-arginine coding sequence is located on the 5' side of the polyproline-coding sequence;

c) assaying the plurality of protein variants for the biological activity; and d) selecting one or more displayed protein variants that have the biological activity.

30. A method of performing directed evolution of a protein, the method comprising:

a) providing a plurality of double stranded DNA templates comprising a library of gene variants encoding a plurality of protein variants;

b) displaying the plurality of protein variants according to the method of claim 1, wherein each double stranded DNA template comprises:

i) a promoter operably linked to an open reading frame (ORF) encoding a protein variant of said library;

ii) a molecular roadblock that blocks progress of an RNA polymerase during transcription of the DNA template, wherein the roadblock is located at the 5' end of the DNA template antisense strand, or at the 3' end of the DNA template sense strand, or at both the 5' end of the DNA template antisense strand and the 3' end of the DNA template sense strand; and iii) a nucleic acid encoding a ribosome stall sequence, wherein the nucleic acid encoding the ribosome stall sequence is located on the 3' side of the ORF, wherein the ribosome stall sequence comprises:

a polyproline-coding sequence adjacent to a stop codon, wherein the polyproline-coding sequence is located on the 5' side of the stop codon, and an arginine-histidine-arginine coding sequence adjacent to the polyproline-coding sequence, wherein the arginine-histidine-arginine coding sequence is located on the 5' side of the polyproline-coding sequence;

c) assaying the plurality of protein variants for a desired biological activity;

d) selecting displayed protein variants that have a desired biological activity;

e) mutating the DNA sequences of the DNA templates encoding said protein variants that have the biological activity; and f) selecting one or more protein variants encoded by the mutated DNA sequences that have the biological activity to generate a DNA library enriched for DNA templates encoding the one or more protein variants that have the biological activity.

* * * * *

SEQUENCE LISTING

```
<160> NUMBER OF SEQ ID NOS: 17

<210> SEQ ID NO 1
<211> LENGTH: 29
<212> TYPE: DNA
<213> ORGANISM: Artificial Sequence
<220> FEATURE:
<223> OTHER INFORMATION: Adapter C
<220> FEATURE:
<221> NAME/KEY: source
<222> LOCATION: (1)..(29)
<223> OTHER INFORMATION: sequence is synthesized

<400> SEQUENCE: 1
aatgatacgg cgaccaccga gatctacac                               29

<210> SEQ ID NO 2
<211> LENGTH: 24
<212> TYPE: DNA
<213> ORGANISM: Artificial Sequence
<220> FEATURE:
<223> OTHER INFORMATION: Adapter D
<220> FEATURE:
<221> NAME/KEY: source
<222> LOCATION: (1)..(24)
<223> OTHER INFORMATION: sequence is synthesized

<400> SEQUENCE: 2
caagcagaag acggcatacg agat                                    24

<210> SEQ ID NO 3
<211> LENGTH: 19
<212> TYPE: DNA
<213> ORGANISM: Artificial Sequence
<220> FEATURE:
<223> OTHER INFORMATION: E. coli RNAP holoenzyme-specific promoter
```

<400> SEQUENCE: 3
tttatgctat aattatttc                                                    19

<210> SEQ ID NO 4
<211> LENGTH: 39
<212> TYPE: DNA
<213> ORGANISM: Artificial Sequence
<220> FEATURE:
<223> OTHER INFORMATION: Template with stall sequence
<220> FEATURE:
<221> NAME/KEY: source
<222> LOCATION: (1)..(39)
<223> OTHER INFORMATION: sequence is synthesized

<400> SEQUENCE: 4
atgtagtaag gaggttgtat ggaagacgtt cctggatcc                              39

<210> SEQ ID NO 5
<211> LENGTH: 31
<212> TYPE: DNA
<213> ORGANISM: Artificial Sequence
<220> FEATURE:
<223> OTHER INFORMATION: Pre-ribosomal binding site spacer sequence
<220> FEATURE:
<221> NAME/KEY: source
<222> LOCATION: (1)..(31)
<223> OTHER INFORMATION: sequence is synthesized

<400> SEQUENCE: 5
ccctctagaa ataattttgt ttaactttaa g                                      31

<210> SEQ ID NO 6
<211> LENGTH: 27
<212> TYPE: DNA
<213> ORGANISM: Artificial Sequence
<220> FEATURE:
<223> OTHER INFORMATION: linker
<220> FEATURE:
<221> NAME/KEY: source
<222> LOCATION: (1)..(27)
<223> OTHER INFORMATION: sequence is synthesized

<400> SEQUENCE: 6
ggaagcacag gagagaaggg caagcag                                           27

<210> SEQ ID NO 7
<211> LENGTH: 9
<212> TYPE: PRT
<213> ORGANISM: Artificial Sequence
<220> FEATURE:
<223> OTHER INFORMATION: linker

<400> SEQUENCE: 7

Gly Ser Thr Gly Glu Lys Gly Lys Gln
1               5

<210> SEQ ID NO 8
<211> LENGTH: 147
<212> TYPE: DNA
<213> ORGANISM: Artificial Sequence
<220> FEATURE:
<223> OTHER INFORMATION: Small computationally designed thermostable
      3-helix bundle linker
<220> FEATURE:
<221> NAME/KEY: source
<222> LOCATION: (1)..(147)
<223> OTHER INFORMATION: sequence is synthesized

<400> SEQUENCE: 8
aagcagtggt cagagaacgt cgaagaaaaa ctcaaggaat tcgtgaaacg acatcagcgg    60
atcacccagg aggagctgca ccaatatgct caacgactgg gattgaacga agaggcgatt   120
agacagttct ttgaggagtt cgagcaa                                      147

<210> SEQ ID NO 9
<211> LENGTH: 49
<212> TYPE: PRT
<213> ORGANISM: Artificial Sequence
<220> FEATURE:
<223> OTHER INFORMATION: small computationally designed thermostable
      3-helix bundle linker

<400> SEQUENCE: 9

Lys Gln Trp Ser Glu Asn Val Glu Glu Lys Leu Lys Glu Phe Val Lys
1               5                   10                  15

Arg His Gln Arg Ile Thr Gln Glu Glu Leu His Gln Tyr Ala Gln Arg
            20                  25                  30

Leu Gly Leu Asn Glu Glu Ala Ile Arg Gln Phe Phe Glu Glu Phe Glu
        35                  40                  45

Gln

<210> SEQ ID NO 10
<211> LENGTH: 60
<212> TYPE: DNA
<213> ORGANISM: Artificial Sequence
<220> FEATURE:
<223> OTHER INFORMATION: Ribosome/RNAP stall footprint

<400> SEQUENCE: 10
agaaagggag acggaacaaa gtccggcggt ctttgcatcc tggctgcgtg cataattgct    60

<210> SEQ ID NO 11
<211> LENGTH: 27
<212> TYPE: PRT
<213> ORGANISM: Artificial Sequence
<220> FEATURE:
<223> OTHER INFORMATION: Translated amino acid sequence of stall
      sequence
<220> FEATURE:
<221> NAME/KEY: misc_feature
<222> LOCATION: (24)..(24)
<223> OTHER INFORMATION: Xaa can be any naturally occurring amino acid

<400> SEQUENCE: 11

Lys Glu Ala Ala Ala Lys Phe Ser Thr Lys Trp Trp Ile Ile Asp Lys
1               5                   10                  15

Trp Arg His Arg Pro Pro Pro Xaa Arg Leu Thr
            20                  25

<210> SEQ ID NO 12
<211> LENGTH: 81
<212> TYPE: DNA
<213> ORGANISM: Artificial Sequence
<220> FEATURE:
<223> OTHER INFORMATION: DNA template with stall sequence (Example 2)
<220> FEATURE:
<221> NAME/KEY: source
<222> LOCATION: (1)..(81)
<223> OTHER INFORMATION: sequence is synthesized

<400> SEQUENCE: 12
aaagaagcag ctgcaaagtt cagcacgaaa tggtggataa ttgacaaatg gcgccaccgt    60
ccgccacctt agcgcctcac c                                             81

<210> SEQ ID NO 13
<211> LENGTH: 50
<212> TYPE: DNA
<213> ORGANISM: Escherichia coli

<400> SEQUENCE: 13
tatcaaaaag agtattgact taaagtctaa cctataggat acttacagcc        50

<210> SEQ ID NO 14
<211> LENGTH: 39
<212> TYPE: DNA
<213> ORGANISM: Artificial Sequence
<220> FEATURE:
<223> OTHER INFORMATION: optimized Shine Dalgarno sequence
<220> FEATURE:
<221> NAME/KEY: source
<222> LOCATION: (1)..(39)
<223> OTHER INFORMATION: sequence is synthesized

<400> SEQUENCE: 14
agaaataatt ttgtttaact ttaagaagga gatatacat        39

<210> SEQ ID NO 15
<211> LENGTH: 27
<212> TYPE: PRT
<213> ORGANISM: Artificial Sequence
<220> FEATURE:
<223> OTHER INFORMATION: SecM

<400> SEQUENCE: 15

Phe Thr Pro Gln Ala Lys Phe Ser Thr Pro Val Trp Ile Ser Gln Ala
1               5                   10                  15

Gln Gly Ile Arg Ala Gly Pro Gln Arg Leu Thr
            20                  25

<210> SEQ ID NO 16
<211> LENGTH: 27
<212> TYPE: PRT
<213> ORGANISM: Artificial Sequence
<220> FEATURE:
<223> OTHER INFORMATION: TnaC
<220> FEATURE:
<221> NAME/KEY: misc_feature
<222> LOCATION: (24)..(24)
<223> OTHER INFORMATION: Xaa can be any naturally occurring amino acid

<400> SEQUENCE: 16

Asn Ile Leu His Ile Cys Val Thr Ser Lys Trp Phe Asn Ile Asp Asn
1               5                   10                  15

Lys Ile Val Asp His Arg Pro Xaa Phe Ala Leu
            20                  25

<210> SEQ ID NO 17
<211> LENGTH: 27
<212> TYPE: PRT
<213> ORGANISM: Artificial Sequence
<220> FEATURE:
<223> OTHER INFORMATION: CJL-PPP
<220> FEATURE:
<221> NAME/KEY: misc_feature
<222> LOCATION: (24)..(24)
<223> OTHER INFORMATION: Xaa can be any naturally occurring amino acid

```
<400> SEQUENCE: 17

Lys Glu Ala Ala Ala Lys Phe Ser Thr Lys Trp Trp Ile Ile Asp Lys
1               5                   10                  15

Trp Arg His Arg Pro Pro Pro Xaa Phe Ala Leu
            20                  25
```